(12) United States Patent
Rong et al.

(10) Patent No.: US 11,942,191 B2
(45) Date of Patent: Mar. 26, 2024

(54) COMPOUND PROPERTY PREDICTION METHOD AND APPARATUS, COMPUTER DEVICE, AND READABLE STORAGE MEDIUM

(71) Applicant: TENCENT TECHNOLOGY (SHENZHEN) COMPANY LIMITED, Shenzhen (CN)

(72) Inventors: Yu Rong, Shenzhen (CN); Wenbing Huang, Shenzhen (CN); Tingyang Xu, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 593 days.

(21) Appl. No.: 17/168,162

(22) Filed: Feb. 4, 2021

(65) Prior Publication Data
US 2021/0158904 A1    May 27, 2021

Related U.S. Application Data

(63) Continuation of application No. PCT/CN2020/117433, filed on Sep. 24, 2020.

(30) Foreign Application Priority Data

Oct. 15, 2019    (CN) .......................... 201910979509.8

(51) Int. Cl.
G16C 20/50    (2019.01)
G06N 3/048    (2023.01)
(Continued)

(52) U.S. Cl.
CPC ............. *G16C 20/30* (2019.02); *G06N 3/048* (2023.01); *G06N 3/08* (2013.01); *G16C 20/50* (2019.02); *G16C 20/70* (2019.02)

(58) Field of Classification Search
CPC .......... G06N 3/048; G06N 3/08; G16C 20/30; G16C 20/50; G16C 20/70
See application file for complete search history.

(56) References Cited

U.S. PATENT DOCUMENTS 6,957,151 B2 * 10/2005 Cheng .................... G01N 33/15
   702/30
11,087,861 B2 * 8/2021 Takeda ................... G16C 20/20
2018/0276346 A1    9/2018 Grzybowski et al.
2019/0286791 A1    9/2019 Takeda et al.

FOREIGN PATENT DOCUMENTS

CN    107563121 A    1/2018
CN    109461475 A    3/2019
(Continued)

OTHER PUBLICATIONS

Fei et al., "Structure Feature Selection for Chemical Compound Classification", 2008, IEEE, pp. 1-6 (Year: 2008).*
(Continued)

*Primary Examiner* — Elias Desta
(74) *Attorney, Agent, or Firm* — ANOVA LAW GROUP, PLLC

(57) ABSTRACT

A compound property prediction method is provided for an electronic device. The method includes obtaining chemical structure information of a target compound, the chemical structure information including an atom and a chemical bond, modeling a chemical structure graph according to the chemical structure information, the chemical structure graph including a first node corresponding to the atom and a first edge corresponding to the chemical bond, constructing an original node feature of the first node and an original edge feature of the first edge, performing a message propagation on the first edge according to the original node feature of the first node and the original edge feature of the first edge to obtain propagation state information of the first edge, and (Continued)

predicting properties of the target compound according to the propagation state information of the first edge.

20 Claims, 15 Drawing Sheets

(51) Int. Cl.
*G06N 3/08* (2023.01)
*G16C 20/30* (2019.01)
*G16C 20/70* (2019.01)

(56) References Cited

FOREIGN PATENT DOCUMENTS

| CN | 110263780 | A | 9/2019 |
|----|-----------|---|--------|
| CN | 110277144 | A | 9/2019 |
| JP | 2019095957 | A | 6/2019 |
| WO | 2019186194 | A2 | 10/2019 |

OTHER PUBLICATIONS

The World Intellectual Property Organization (WIPO) International Search Report for PCT/CN2020/117433 dated Dec. 23, 2020 8 Pages (including translation).
Peter Bjorn Jorgensen et al., "Neural Message Passing with Edge Updates for Predicting Properties of Molecules and Materials," arXiv:1806.03146, Jun. 8, 2018 (Jun. 8, 2018), pp. 1-10. 10 pages.
The State Intellectual Property Office of the People's Republic of China (SIPO) Office Action 1 for 201910979509.8 dated Aug. 26, 2020 18 Pages (including translation).
Xiaodong Wang, "Predicting Properties of Compound Based on Graph Mining," China Master's Theses Full-text Database, Engineering Science and Technology, 01 period, Jan. 15, 2019 (Jan. 15, 2019), pp. 1-16. 53 pages.
Jia Li et al, "Semi-Supervised Graph Classification: A Hierarchical Graph Perspective," arXiv:1904.05003, Apr. 10, 2019 (Apr. 10, 2019), p. 1-11. 11 pages.
Justin Gilmer et al., "Neural Message Passing for Quantum Chemistry", arXiv:1704.01212, Jun. 12, 2017 (Jun. 12, 2017), pp. 1-14. 14 pages.

\* cited by examiner

Molecule: (C10H4N2)

COMPOUND PROPERTY PREDICTION METHOD AND APPARATUS, COMPUTER DEVICE, AND READABLE STORAGE MEDIUM

RELATED APPLICATION

This application is a continuation application of PCT Patent Application No. PCT/CN2020/117433, filed on Sep. 24, 2020, which claims priority to Chinese Patent Application No. 201910979509.8, entitled "COMPOUND PROPERTY PREDICTION METHOD AND APPARATUS, COMPUTER DEVICE, AND READABLE STORAGE MEDIUM" filed with the China National Intellectual Property Administration on Oct. 15, 2019, all of which are incorporated by reference in entirety.

FIELD OF THE TECHNOLOGY

The present disclosure relates to the field of artificial intelligence (AI) technologies, and more particularly, to a compound property prediction method and apparatus, a computer device, and a readable storage medium.

BACKGROUND

In the pharmaceutical analysis, how to determine or predict, according to the structure of a compound such as protein, certain properties of the compound including chemical and biological properties such as toxicity, solubility, and carcinogenicity is often a very important task.

Certain existing compound property prediction procedures are implemented through AI. For example, such a task as property prediction may be modeled into a classification problem in AI machine learning. Specifically, a structural formula of a compound such as protein may be converted into a vector in Euclidean space in a manner of representation learning, and then the vector is classified by using a neural network such as a convolutional neural network (CNN) to determine or predict properties of the substance such as chemical/biological properties.

As a classic method of the representation learning, the CNN has achieved great success in the field of identification and the like.

SUMMARY

One aspect of the present disclosure provides a compound property prediction method. The method includes obtaining chemical structure information of a target compound, the chemical structure information including an atom and a chemical bond, modeling a chemical structure graph according to the chemical structure information, the chemical structure graph including a first node corresponding to the atom and a first edge corresponding to the chemical bond, constructing an original node feature of the first node and an original edge feature of the first edge, performing a message propagation on the first edge according to the original node feature of the first node and the original edge feature of the first edge to obtain propagation state information of the first edge, and predicting properties of the target compound according to the propagation state information of the first edge.

Another aspect of the present disclosure provides a compound property prediction apparatus, including a memory and a processor coupled to the memory. The processor is positioned to perform obtaining chemical structure information of a target compound, the chemical structure information including an atom and a chemical bond, modeling a chemical structure graph according to the chemical structure information, the chemical structure graph including a first node corresponding to the atom and a first edge corresponding to the chemical bond, constructing an original node feature of the first node and an original edge feature of the first edge, performing a message propagation on the first edge according to the original node feature of the first node and the original edge feature of the first edge to obtain propagation state information of the first edge, and predicting properties of the target compound according to the propagation state information of the first edge.

Yet another aspect of the present disclosure provides a non-transitory computer-readable storage medium. The non-transitory computer-readable storage medium stores computer program instructions executable by at least one processor to perform obtaining chemical structure information of a target compound, the chemical structure information including an atom and a chemical bond, modeling a chemical structure graph according to the chemical structure information, the chemical structure graph including a first node corresponding to the atom and a first edge corresponding to the chemical bond, constructing an original node feature of the first node and an original edge feature of the first edge, performing a message propagation on the first edge according to the original node feature of the first node and the original edge feature of the first edge to obtain propagation state information of the first edge, and predicting properties of the target compound according to the propagation state information of the first edge.

Other aspects of the present disclosure can be understood by those skilled in the art in light of the description, the claims, and the drawings of the present disclosure.

BRIEF DESCRIPTION OF THE DRAWINGS

To more clearly describe technical solutions of certain embodiments of the present disclosure, described below are accompanying drawings. The accompanying drawings are illustrative of certain embodiments of the present disclosure, and a person skilled in the art may still derive other drawings from these accompanying drawings without creative efforts.

FIG. 2f to FIG. 2l are schematic flowcharts of a compound property prediction method according to one or more embodiments of the present disclosure;

FIG. 6b is a schematic structural diagram of a blockchain and blocks in the data sharing system shown in FIG. 6a.

DETAILED DESCRIPTION

Figure 1:
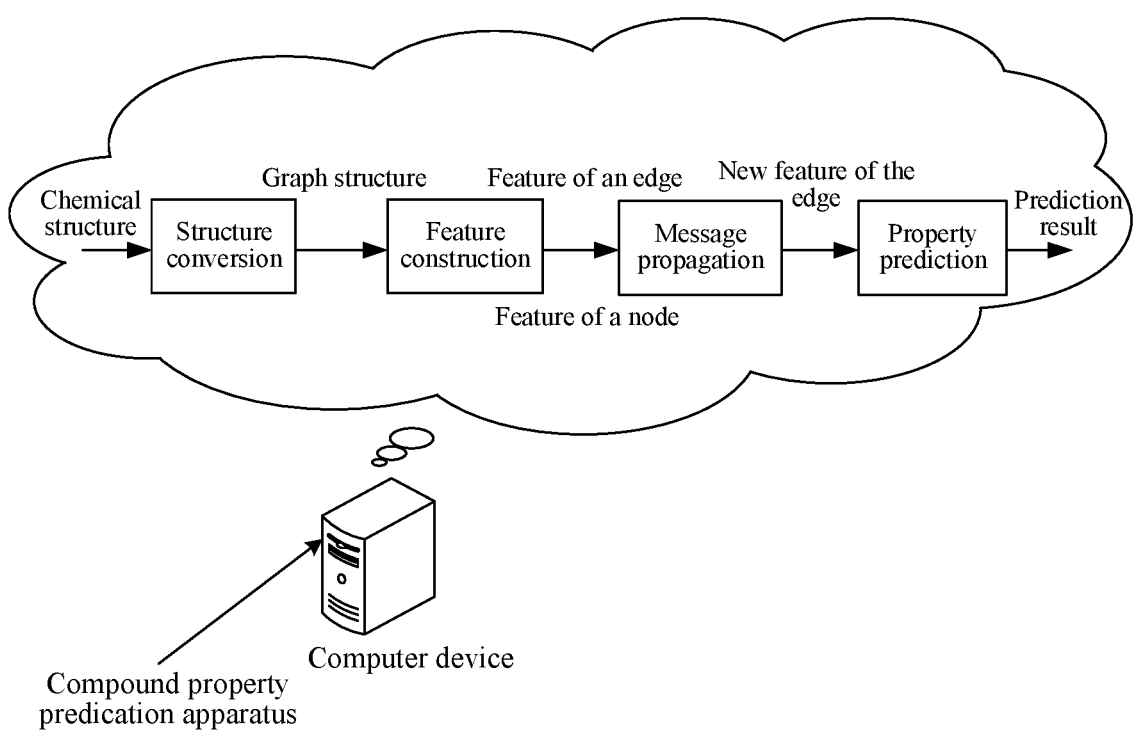
FIG. 1 is a schematic diagram of a scenario of a compound property prediction method according to one or more embodiments of the present disclosure.

The technical solutions in certain embodiments of present disclosure are clearly described in the following with reference to the accompanying drawings in the embodiments of present disclosure. Apparently, the described embodiments are merely some embodiments of present disclosure rather than all of the embodiments. All other embodiments obtained by a person skilled in the art based on the embodiments of present disclosure without creative efforts shall fall within the protection scope of present disclosure.

Several existing models and architectures are used for resolving problems of large-scale classification and recognition. Specific implementations include image processing, natural language processing, and the like. However, source data of these implementations has one thing in common, that is, has a grid structure. However, a chemical structure of a compound such as protein does not have such a grid structure, which leads to lower accuracy of property prediction.

In certain embodiments of the present disclosure, chemical structure information of a target compound is obtained, where the chemical structure information includes an atom and a chemical bond; a chemical structure graph corresponding to the chemical structure information is modeled or generated according to the chemical structure information, where the chemical structure graph includes a node corresponding to the atom and an edge corresponding to the chemical bond, where the node may be termed a first node and the edge may be termed a first edge when a plurality of nodes and edges are involved in the chemical structure graph; an original node feature of the node and an original edge feature of the edge are constructed, where an "original" node feature may alternatively be termed a "first" node feature and an "original" edge feature may alternatively be termed a "first" edge feature to indicate such node feature or edge feature is constructed prior to one or more rounds of message propagation; a plurality of rounds of message propagation are performed on the edge according to the original node feature of the node and the original edge feature of the edge to obtain propagation state information of the edge after the plurality of rounds of message propagation; a target feature of the edge is obtained according to the propagation state information; and properties of the target compound are predicted according to the target feature of the edge, and a property prediction result of the target compound is outputted. In this solution, a chemical structural formula of a target may be converted into a data structure such as a graph, the feature of the edge corresponding to the chemical bond in the graph is obtained in a manner based on a plurality of times of message propagation on graph data, and the properties of the target compound are predicted based on the feature of the edge. Therefore, the properties of the target compound can be accurately predicted, greatly improving the accuracy of the property prediction.

Certain embodiments of the present disclosure provide a compound property prediction method and apparatus, a computer device, and a computer-readable storage medium. The compound property prediction apparatus may be integrated in the computer device. The computer device may be a server, a terminal, or another device.

The compound property prediction solution provided in certain embodiments of the present disclosure relates to computer vision (CV) technologies of AI. Images may be classified by means of the CV technologies of AI. For example, graphs corresponding to chemical structural formulas are classified.

The CV technology is a science that studies how to use a machine to "see", and furthermore, is machine vision that a camera and a computer are used for replacing human eyes to perform recognition, tracking, measurement, and the like on a target, and further perform graphic processing, so that the computer processes the target into an image more suitable for human eyes to observe, or an image transmitted to an instrument for detection. As a scientific subject, the CV studies related theories and technologies, and attempts to establish an AI system that can obtain information from images or multidimensional data. The CV technologies generally include technologies such as image classification, image recognition, image segmentation, image semantic understanding, image retrieval, optical character recognition (OCR), video processing, video semantic understanding, video content/behavior recognition, three-dimensional object reconstruction, a 3D technology, virtual reality, augmented reality, synchronous positioning, and map construction, and further include biological feature recognition technologies such as common face recognition and fingerprint recognition.

In certain embodiments of the present disclosure, the so-called compound property prediction is to predict properties or attributes of a certain compound, for example, to predict chemical properties or biological properties of the compound such as toxicity, solubility, and carcinogenicity of the compound. Specifically, the compound property prediction may include obtaining a property classification result of the compound by performing property classification on graph structure data corresponding to the target.

For example, referring to FIG. 1, the compound property prediction apparatus integrated in a computing device is used as an example. The computing device, which may alternatively be termed the "computer" device, and which may be a desktop and handheld computer, may obtain chemical structure information of a target such as a chemical structural formula, where the chemical structure information includes an atom and a chemical bond; generate a chemical structure graph corresponding to the chemical structure information according to the chemical structure information, where the chemical structure graph may include a node corresponding to the atom and an edge corresponding to the chemical bond; construct an original node feature of the node and an original edge feature of the edge; perform a plurality of rounds of message propagation on the edge according to the original node feature of the node and the original edge feature of the edge to obtain propagation state information of the edge after the plurality of rounds of message propagation; obtain a target feature of the edge according to the propagation state information; and predict properties of the target compound according to the target feature of the edge, and output a property prediction result of the target compound. For example, chemical or biological properties (such as toxicity, solubility, and hydrophilicity) of the target compound may be predicted.

Figure 6A:
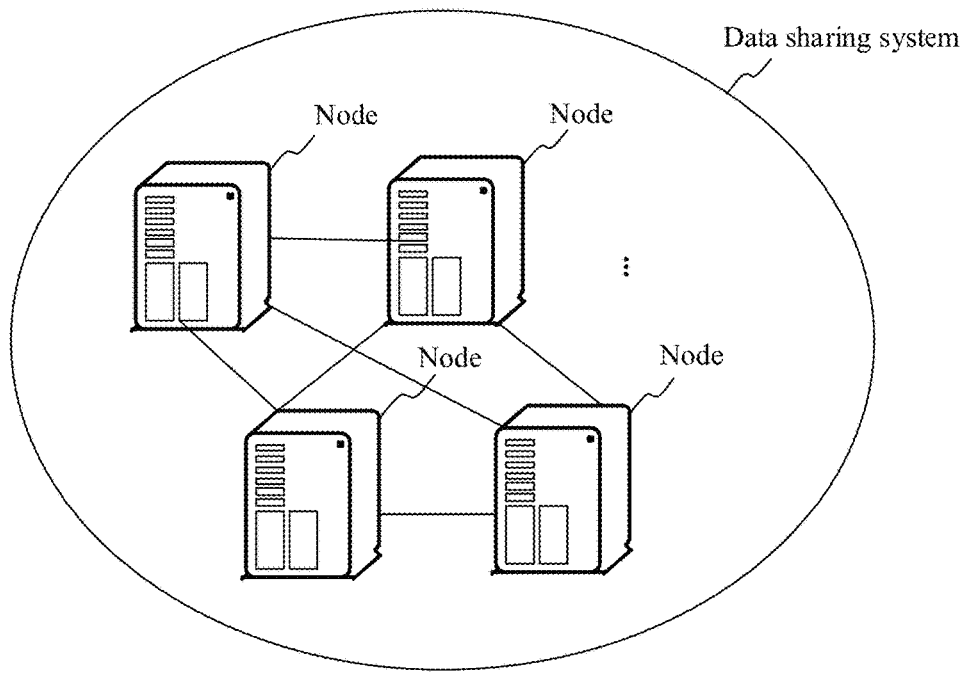
FIG. 6a is a schematic structural diagram of a data sharing system according to one or more embodiments of the present disclosure.

In some embodiments, referring to FIG. 6a, the computing device may be a node in a data sharing system. The data sharing system is a system used for performing data sharing between nodes. The data sharing system may include a plurality of nodes, and the plurality of nodes may be network devices in the data sharing system. One blockchain is stored in each node, and the blockchains in the nodes are all the same. The compound property prediction apparatus may store a property prediction result in the blockchain to perform data sharing with other network devices.

The example in FIG. 1 is merely an example of a system architecture for implementing the embodiments of present disclosure, and the embodiments of present disclosure are not limited to the system architecture shown in FIG. 1. The embodiments of present disclosure are proposed based on the system architecture shown in FIG. 1.

Detailed descriptions are separately provided below. The description sequence of the following embodiments is not intended to limit preference orders of the embodiments.

This embodiment is described from the perspective of the compound property prediction apparatus. The compound property prediction apparatus may be specifically integrated in the computing device, and the computing device may be a server, a terminal, or another device. The terminal may include a tablet computer, a notebook computer, a personal computer (PC), a micro processing box, or another device.

Figure 2A:
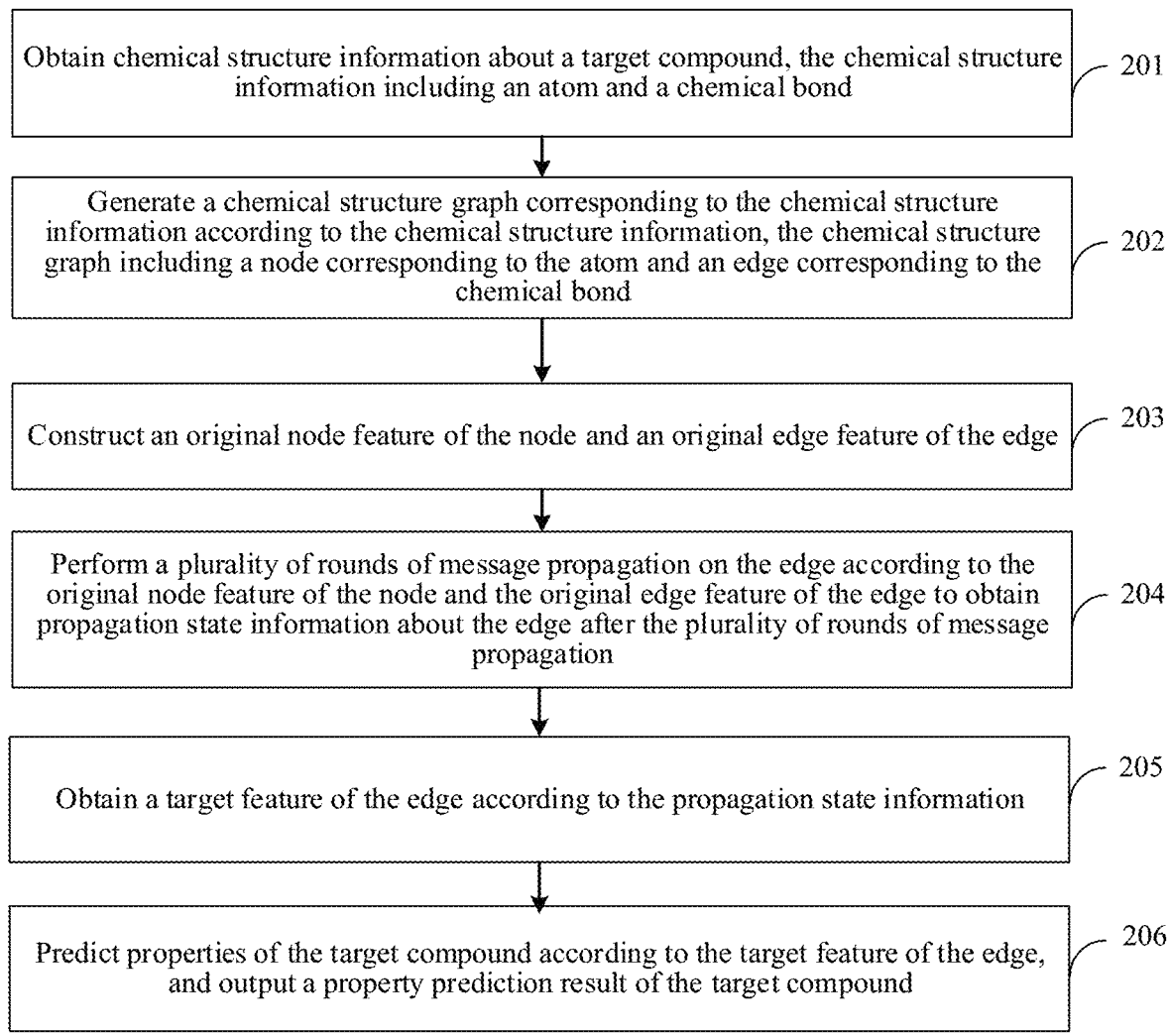
FIG. 2a is a flowchart of a compound property prediction method according to one or more embodiments of the present disclosure.

As shown in FIG. 2a, a specific process of the compound property prediction method may be as follows:

201. Obtain chemical structure information of a target compound, the chemical structure information including an atom and a chemical bond.

The compound may be a pure substance composed of two or more different elements (different from an elementary substance). The compound has certain characteristics, which are not only different from those of elements or ions contained in the compound, but also different from those of other compounds. The compound usually further has a certain composition. In some embodiments, the compound may further include a life compound such as protein.

The chemical structure information of the compound is information for representing a chemical composition structure of the compound, and may include, for example, a chemical structural formula.

Figure 2B:
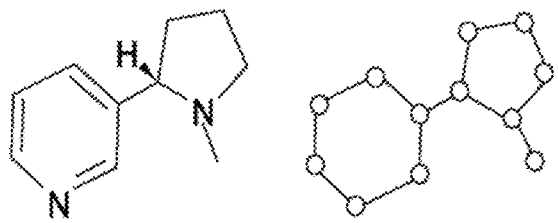
FIG. 2b is a schematic diagram of conversion of a chemical structure graph according to one or more embodiments of the present disclosure.

The chemical structural formula is a chemical composition formula using element symbols and short lines to represent permutation and combination manners of atoms in molecules of a substance such as a compound (or an elementary substance), which is a method for simply describing a molecular structure. Generally, the chemical structural formula may be formed by atoms and chemical bonds. For example, the left figure in FIG. 2b is the chemical structural formula of a nicotine molecule (C10H4N2).

In certain embodiments of present disclosure, there are a plurality of manners of obtaining the chemical structure information of the target. For example, the chemical structure information may be inputted by a user, or may be extracted from a database.

202. Generate a chemical structure graph corresponding to the chemical structure information according to the chemical structure information, the chemical structure graph including a node corresponding to the atom and an edge corresponding to the chemical bond.

For example, in some embodiments, the chemical structure information may be converted into the corresponding chemical structure graph.

For improving accuracy and efficiency of the property prediction or classification, in certain embodiments of the present disclosure, the chemical structure information, such as the chemical structural formula, of the target compound may be converted into the data structure such as the graph, that is, the chemical structure graph, and a prediction method based on a neural network is constructed on the graph data to predict properties of the target compound.

The chemical structure graph may be formed by nodes and edges. The node in the graph corresponds to the atom in the chemical structure information (such as the chemical structural formula), and the edge (that is, connecting line) in the graph corresponds to the chemical bond in the chemical structure information (such as the chemical structural formula).

Specifically, atoms in the chemical structure information (such as the chemical structural formula) may serve as virtual nodes, and the virtual nodes are connected according to chemical bonds between the atoms to obtain the chemical structure graph.

For example, referring to FIG. 2b, the nicotine molecule (C10H4N2) may be represented in a chemical structure graph of the nicotine molecule shown in the right figure in FIG. 2b, where the atom is the node in the graph, and the chemical bond is the edge in the graph.

203. Construct an original node feature of the node and an original edge feature of the edge.

In certain embodiments of the present disclosure, there are a plurality of representation forms of the feature, for example, a vector form. For example, an original node feature vector of the node and an original edge feature vector of the edge may be constructed.

The sequence between step 203 and step 202 is not limited by the sequence numbers. Step 203 may be performed simultaneously with or may be performed before step 202, which may be specifically set according to actual requirements.

In some embodiments, the original node feature of the node is constructed according to attribute information of the atom, and the original edge feature of the edge is constructed according to attribute information of the chemical bond.

The attribute information of the atom may include a charge number, a proton number, a neutron number, and the like. In certain embodiments of the present disclosure, the attribute of the atom such as the charge number, the proton number, or the neutron number may be modeled into the feature vector of the atom, and the feature vector of the atom may serve as the feature vector of the node corresponding to the atom in the graph.

The attribute information of the chemical bond may include a chemical bond type, a chemical bond valence state, and the like. In an embodiment of present disclosure, the attribute of the chemical bond may be modeled into the feature vector of the edge corresponding to the chemical bond.

In certain embodiments of the present disclosure, a graph may be defined as: $G(V, E)$, where V represents a node set, and E represents an edge set. Both the nodes and edges in the graph may have their own feature vectors. In addition, in certain embodiments of the present disclosure, $x_v$ represents the feature vector of the node v, and $e_{vw}$ represents the feature vector of the edge vw (without causing confusion, E may also be used to represent an edge feature set. Such a data structure may conveniently represent chemical molecules.

204. Perform a plurality of rounds of message propagation on the edge according to the original node feature of the node and the original edge feature of the edge to obtain propagation state information of the edge after the plurality of rounds of message propagation.

The message propagation on the edge in the graph is taking each edge in the chemical structure graph as an entity, taking each node as a connection between edges, and propagating information of the edges through a common node of the edges. When a plurality of nodes are involved, and according to certain embodiments of the present disclosure, the term "each node" refers to one or more nodes.

In certain embodiments of present disclosure, edge-related information of the edge is integrated through a plurality of rounds of iterative message propagation on the edge in the chemical structure graph, to construct the feature information of the edge, thereby improving the accuracy of the property prediction. Because properties of the substance such as the compound are often related to the existing chemical bond, and the essence of many chemical reactions is actually breaking and recombination of the chemical bond, the properties of the target compound may be accurately predicted based on the feature information of the chemical bond, greatly improving the accuracy of the property prediction. However, when prediction based on the feature information of the chemical bond is performed, how to obtain accurate feature information of the chemical bond is a problem. For the problem, in certain embodiments of the present disclosure, information of the chemical bond and information of other associated chemical bonds are obtained through the plurality of rounds of message propagation on the edge to construct the feature information of the chemical bond to perform property prediction, which may further improve the accuracy of the property prediction.

The propagation state information of each edge after the plurality of rounds of message propagation in the chemical structure graph may be obtained through the plurality of rounds of iterative message propagation on the edge.

In some embodiments, initial input information is first obtained according to the original node feature and the original edge feature, and then the plurality of rounds of message propagation are performed on the edge based on the initial input information. That is, as shown in FIG. 2f, step 204 may include the following:

S41. Obtain initial input information of the plurality of rounds of message propagation according to the original node feature of the node and the original edge feature of the edge.

S42. Perform the plurality of rounds of message propagation on the edge based on the initial input information to obtain the propagation state information of the edge after the plurality of rounds of message propagation.

In some embodiments, the initial input information may include the propagation state information of the edge during the first round or zeroth round of message propagation, which may be calculated through the original edge feature of the edge and the original node feature of the node on the edge. Specifically, the original edge feature of the edge is aggregated with the original node feature of the node on the edge according to an aggregation parameter to obtain an aggregated edge feature of the edge; and the aggregated edge feature is processed based on an activation function to obtain the initial input information.

For example, the initial input information is defined as the propagation state information $h_{vw}^{(0)}$ of the edge vw during the zeroth round of message propagation. In this case, the propagation state information $h_{vw}^{(0)}$ may be obtained through calculation by using the following formula:

$$h_{vw}^{(0)} = \sigma(W_{in} \text{concat}(e_{vw}, x_v, x_w))$$

where $\sigma(\cdot)$ represents the activation function, concat represents a concatenation function, that is, concatenating three vectors together, and $$W_{in} \in R^{d_{h_{vw}^{(t+1)}} \times (d_{e_{vw}} + d_{x_v} + d_{x_w})}$$

represents the aggregation parameter or an input parameter.

In certain embodiments of present disclosure, there are a plurality of manners of performing the plurality of rounds of message propagation on the edge based on the initial input information, for example, a manner of iterative message propagation based on node information sharing. Specifically, in some embodiments, as shown in FIG. 2f, step S42 may include the following:

S421. Use the initial input information as current input of a current round of message propagation, and perform the current round of message propagation based on the current input.

S422. Obtain current propagation state information of the edge during the current round of message propagation according to the original node feature of the node, a current edge feature of the edge, and historical propagation state information, the historical propagation state information being propagation state information of the edge during a historical round of message propagation.

S423. Update the current input according to the current propagation state information and the original node feature of the node at the time of entering a next round of message propagation, and return to perform the operation of performing the current round of message propagation based on the current input until all rounds of message propagation are completed, to obtain the propagation state information of the edge after the plurality of rounds of message propagation.

The historical propagation state information may be the propagation state information of the edge during the historical round of message propagation. For example, the historical round of message propagation may be set according to actual requirements, and may be, for example, a previous round of message propagation of the current round, previous rounds of message propagation of the current round, or the first round of message propagation.

For example, if t+1 represents the current round of message propagation, the historical round of message propagation may be represented as t, that is, the previous round of message propagation.

According to the description of the above message propagation, using n rounds of message propagation and the edge vw as an example, after the initial state information $h_{vw}^{(0)}$ of the edge vw is calculated, the initial state information $h_{vw}^{(0)}$ and the feature vector set X of the node may serve as input of the first round of message propagation, and the first round of message propagation is performed on the edge vw, to obtain the propagation state information $h_{vw}^{(1)}$ of the edge vw during the first round of message propagation. Then, the propagation state information $h_{vw}^{(1)}$ and the feature vector set X of the node may serve as input of the second round of message propagation, and the second round of message propagation is performed on the edge vw, to obtain the propagation state information $h_{vw}^{(2)}$ of the edge vw during the second round of message propagation, and so on. When the n rounds of message propagation are finished, the propagation state information $h_{vw}^{(n)}$ of the edge vw during the nth round of message propagation may be obtained.

It can be learned that, in certain embodiments of the present disclosure, the feature information of the node is shared among the rounds of message propagation. Therefore, the above message propagation is the message propagation based on the node information sharing. The propagation state information such as $h_{vw}^{(n)}$ on the each edge after the plurality of rounds of message propagation in the chemical structure graph may be obtained through the message propagation based on the node information sharing.

In some embodiments, there are a plurality of manners of obtaining current propagation state information of the edge during the current round of message propagation according to the original node feature of the node, a current edge feature of the edge, and historical propagation state information. For example, for extracting global feature information of the edge and improving the accuracy of prediction, the state information of the edge during the current round of message propagation may be obtained in a manner of integrating the information of the in-edge of the edge.

Figure 2C:
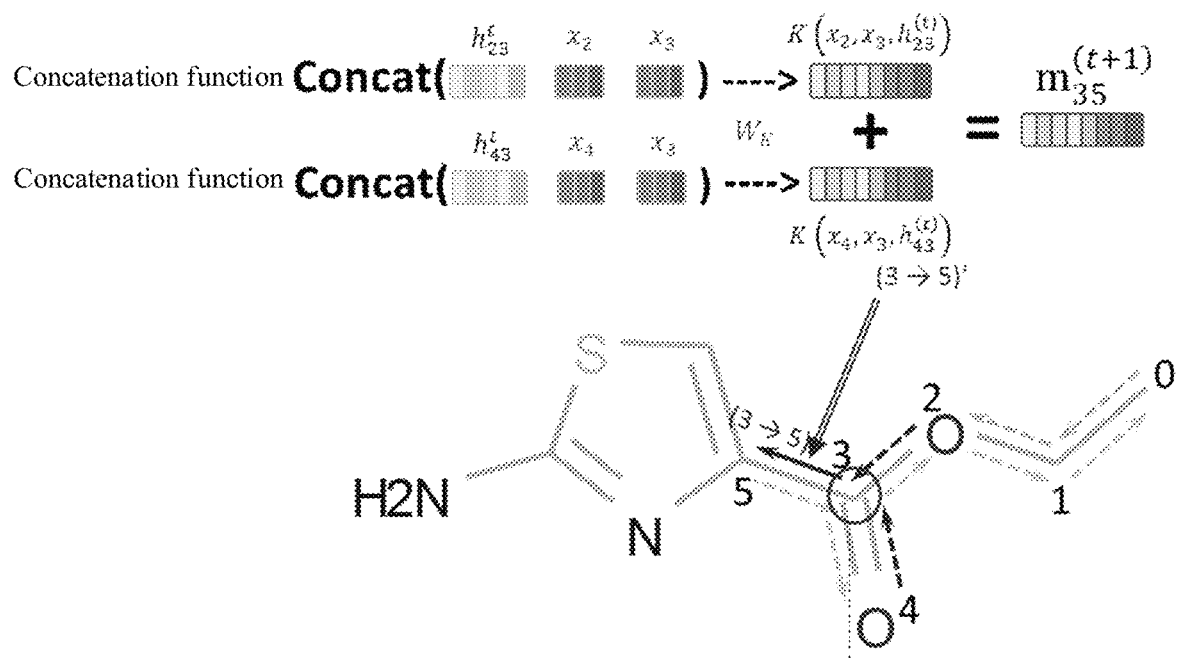
FIG. 2c is a schematic diagram of message propagation calculation according to one or more embodiments of the present disclosure.
Figure 2D:
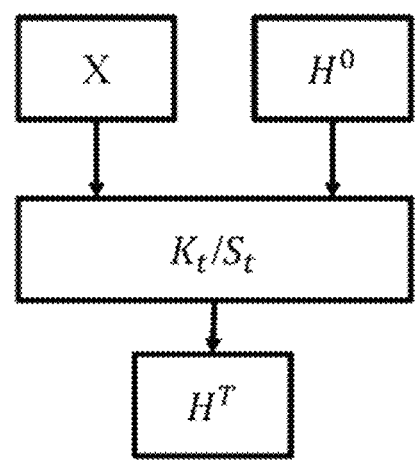
FIG. 2d is a schematic structural diagram of a neural network layer according to one or more embodiments of the present disclosure.
Figure 2E:
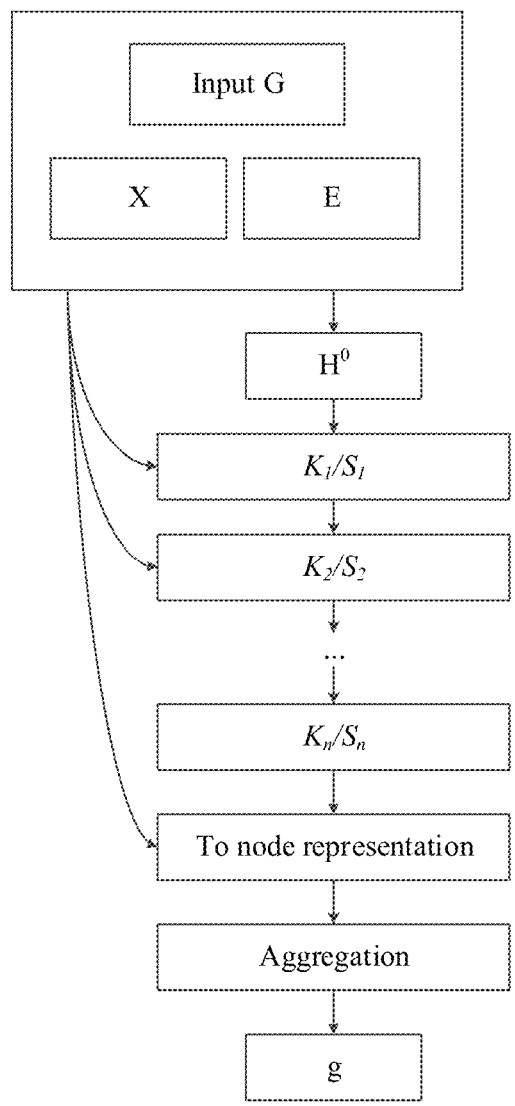
FIG. 2e is a schematic diagram of a network structure of a multi-layer edge information propagation model according to one or more embodiments of the present disclosure.
Figure 2F:
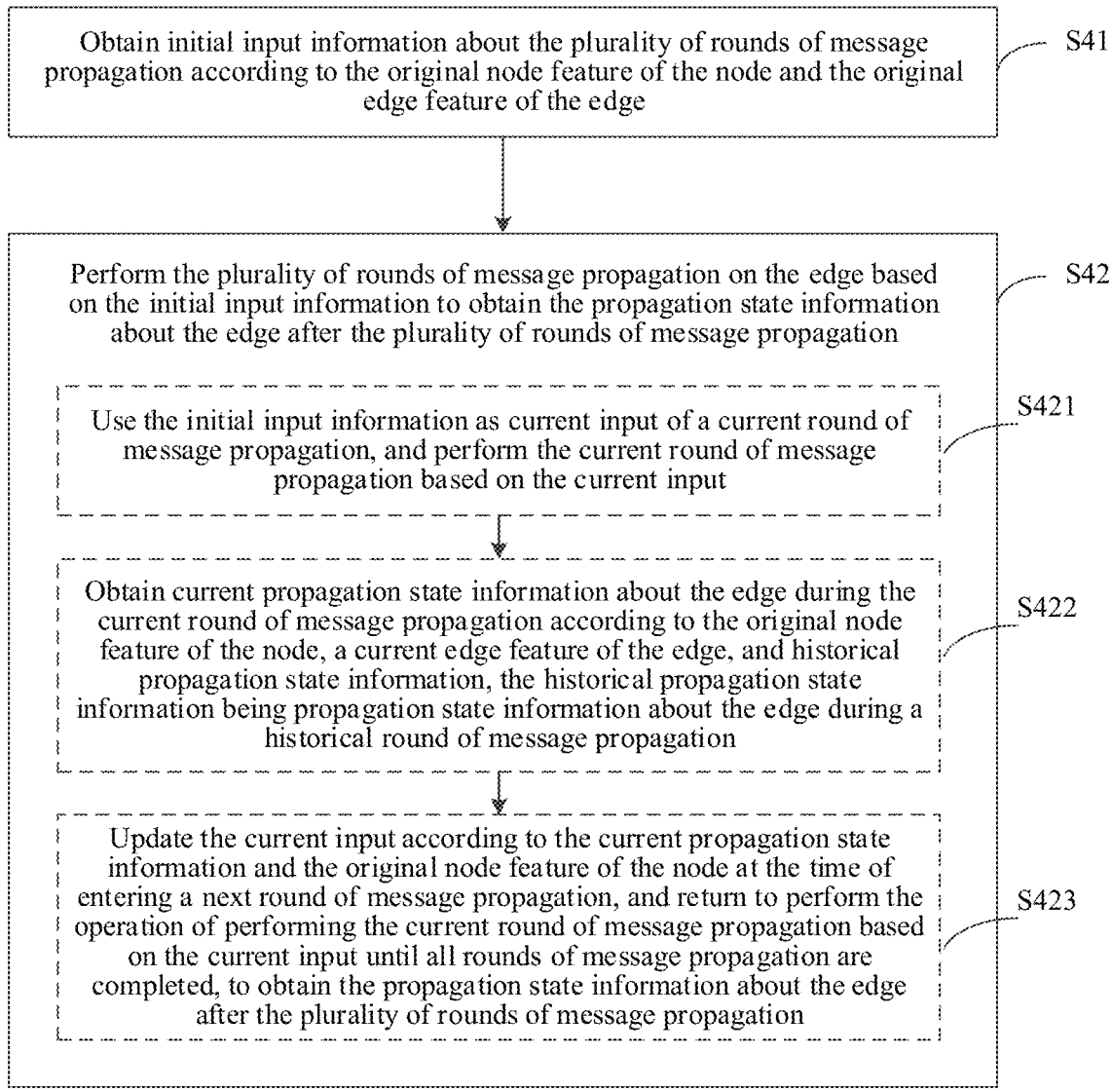
Figure 2G:
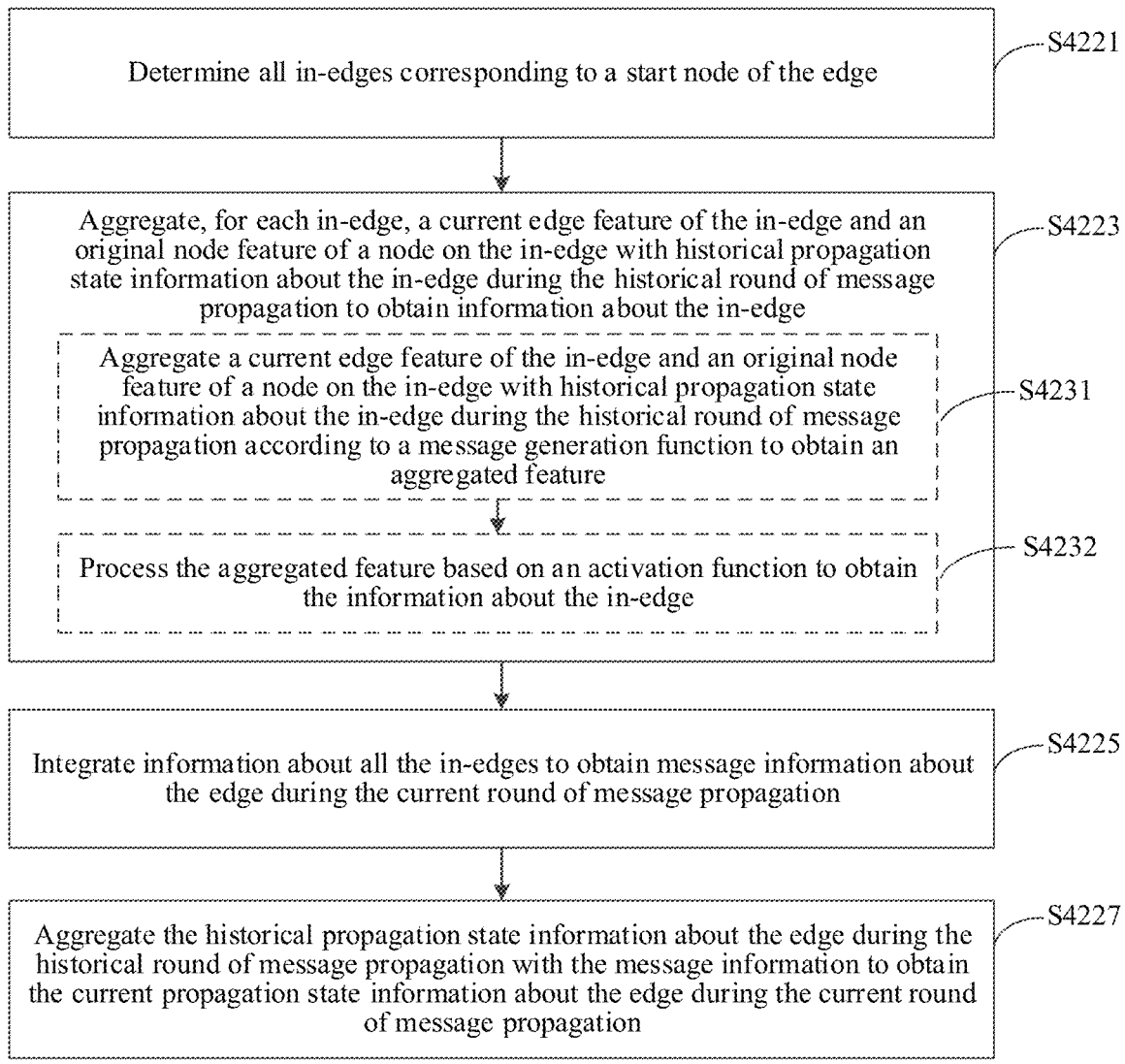

Specifically, as shown in FIG. 2g, step S422 may include the following:

S4221. Determine all in-edges corresponding to a start node of the edge.

S4223. Aggregate, for each in-edge, a current edge feature of the in-edge and an original node feature of a node on the in-edge with historical propagation state information of the in-edge during the historical round of message propagation to obtain information of the in-edge.

S4225. Integrate information of all the in-edges to obtain message information of the edge during the current round of message propagation.

S4227. Aggregate the historical propagation state information of the edge during the historical round of message propagation with the message information to obtain the current propagation state information of the edge during the current round of message propagation.

An in-edge of a certain edge is an in-edge of a start node of the certain edge. The start node is a start node on the certain edge during message propagation. The in-edge of the start node may be a neighboring edge including the start node, for example, an edge whose end node is the start node (that is, a neighboring edge of which a message propagation direction is consistent with a message propagation direction of the edge) in the chemical structure graph. For example, referring to FIG. 2c, the start node of the edge e35 is the node ($v_3$), and the in-edges of the edge e35 include e23 and e43.

Using the edge vw as an example, a process of message propagation based on the edge $e_{vw}$ is defined as the following:

$$m_{vw}^{(t+1)} = \sum_{k \in N(v) \setminus w} K(x_k, x_v, h_{kv}^{(t)})$$

$$h_{vw}^{(t+1)} = S(h_{vw}^{(t)}, m_{vw}^{(t+1)})$$

In the above two formulas, $m_{vw}^{(t)}$ is message information of the edge $e_{vw}$ during the $t^{th}$ round of message propagation, and $h_{vw}^{(t+1)}$ is state information of the edge $e_{vw}$ during the $(t+1)^{th}$ round of message propagation. N(v) is a neighbor set of the node v, K(•) is an edge message generation function, K(•) is an edge state aggregation function, $x_k$ is the feature vector of the node k, and $x_v$ is the feature vector of the node v.

According to the above formulas, the state information $h_{vw}^{(t)}$, on the in-edge kv during the $t^{th}$ round of message propagation and the feature vectors $x_k$ and $x_v$ of the nodes of the in-edge are aggregated to generate the information of each in-edge kv. Then, the information of all in-edges is integrated in a manner of accumulation to obtain the message information $m_{vw}^{(t+1)}$ of the edge vw during the $(t+1)^{th}$ round of message propagation. Next, $m_{vw}^{(t+1)}$ of the edge vw and the state information during the $t^{th}$ round of message propagation are aggregated by using the edge state aggregation function S(•) to obtain the state information of the edge vw during the $(t+1)^{th}$ round of message propagation to further obtain a new feature vector of the edge vw. For example, when the state information is in a vector form, the state information of the edge vw during the $(t+1)^{th}$ round of message propagation may directly serve as the new feature vector of the edge vw.

There are a plurality of manners of message generation of the edge, that is, there are a plurality of manners of aggregating the information of the in-edges. In some embodiments, for improving the accuracy of extracting the edge feature, the aggregation may be performed in the following manner:

Specifically, as shown in FIG. 2g, step S4223 may include the following:

S4231. Aggregate a current edge feature of the in-edge and an original node feature of a node on the in-edge with historical propagation state information of the in-edge during the historical round of message propagation according to a message generation function to obtain an aggregated feature.

S4232. Process the aggregated feature based on an activation function to obtain the information of the in-edge.

For example, the edge message generation function $K_i$ is defined as the following:

$$K(x_k, x_v, h_{kv}^{(t)}) = \sigma(W_K \text{concat}(h_{kv}^{(t)}, x_k, x_v))$$

where σ(•) is the activation function, and generally, the activation function is ReLu(x)=max(0, x), $$\text{Sigmoid}(x) = \frac{1}{1+e^{-x}},$$

or the like; concat is the concatenation function, that is, concatenating three vectors together; and $$W_K \in R^{d_m \times \left(d_{h_{kv}^{(t)}} + d_{x_k} + d_{x_v}\right)}$$

is a parameter of the message generation function.

The message information of the edge vw may be generated by using the message generation function $K(x_k, x_v, h_{kv}^{(t)}) = \sigma(W_K \text{concat}(h_{kv}^{(t)}, x_k, x_v))$, and similarly the information of each in-edge in the graph may be obtained by using the above formula.

For example, referring to FIG. 2c, the above is an example of calculating message propagation. For calculating the message information of the edge $e_{35}$ during the $(t+1)^{th}$ round of message propagation, all the in-edges e43 and e23 of the start node ($v_3$) are first determined.

The message information of the in-edges e43 and e23 is calculated by using the above defined edge message generation function $K_t$. Then, the information of the in-edges e43 and e23 is aggregated, for example, accumulated by using the above defined function of calculating $m_{vw}^{(t)}$, to obtain the message information $m_{35}^{(t+1)}$ on $e_{35}$ during the $(t+1)^{th}$ round of message propagation.

The message information of the edge during the current round of message propagation may be obtained in the above manner. Then, in certain embodiments of the present disclosure, the message information during the current round of message propagation is aggregated with the historical propagation state information during the historical round of message propagation to obtain the current propagation state information of the edge during the current round of message propagation. For example, the message information $m_{vw}^{(t+1)}$ of the edge vw during the $(t+1)^{th}$ round of message propagation may be calculated by using the above formula. Then, the message information $m_{vw}^{(t+1)}$, $m_{vw}^{(t+1)}$ of the edge vw, and the state information of the edge vw during the $t^{th}$ round of message of are aggregated based on the state aggregation function S to obtain the state information $h_{vw}^{(t+1)}$ of the edge vw during the $(t+1)^{th}$ round of message propagation.

The historical round of message propagation is a round of message propagation before the current round, that is, previous message propagation, which may be set according to actual requirements, for example, may be the previous round of message propagation (for example, in certain embodiments of the present disclosure, t+1 represents the current round of message propagation, and t represents the previous round of message propagation), the first round of message propagation, the zeroth round of message propagation, or the like.

Figure 2H:
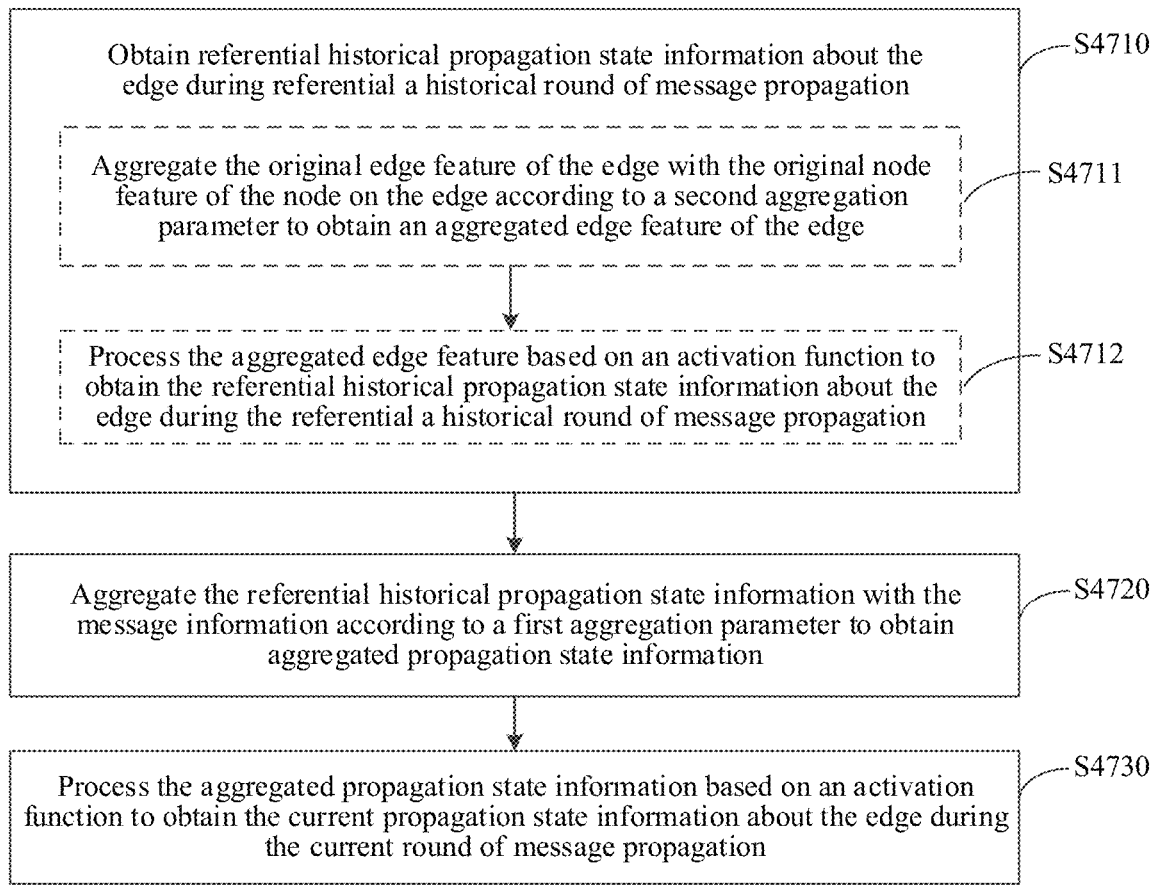

In some embodiments, as shown in FIG. 2h, step S4237 may include the following:

S4710. Obtain referential historical propagation state information of the edge during referential historical round of message propagation.

S4720. Aggregate the referential historical propagation state information with the message information according to a first aggregation parameter to obtain aggregated propagation state information.

S4730. Process the aggregated propagation state information based on an activation function to obtain the current propagation state information of the edge during the current round of message propagation.

The referential historical round of message propagation may be any round of message propagation in previous rounds of message propagation, or may be set according to actual requirements, which is the previous round of message propagation, the first round of message propagation, the zeroth round of message propagation, or the like.

The referential historical round of message propagation being the first round of message propagation is used as an example:

The edge state aggregation function is defined as the following:

$$S(h_{vw}^{(t)}, m_{vw}^{(t+1)}) = \sigma(h_{vw}^{(t)} + W_S m_{vw}^{(t+1)})$$

where $$W_S \in R^{d_{h_{vw}^{(t+1)}} \times d_{m_{vw}^{(t+1)}}}$$

is an aggregation function parameter (corresponding to the above first aggregation parameter).

In some embodiments, there are a plurality manners of obtaining the referential historical propagation state information. For example, as shown in FIG. 2h, step S4710 may include the following:

S4711. Aggregate the original edge feature of the edge with the original node feature of the node on the edge according to a second aggregation parameter to obtain an aggregated edge feature of the edge.

S4712. Process the aggregated edge feature based on an activation function to obtain the referential historical propagation state information of the edge during the referential historical round of message propagation.

The referential historical round of message propagation being the first round or initial round of message propagation is used as an example, where $h_{vw}^0$ is an input state of the edge vw, that is, the state of the first round of message propagation, which is defined as follows: $h_{vw}^{(0)} = \sigma(W_{in} \text{concat}(e_{vw}, x_v, x_w))$, where $$W_{in} \in R^{d_{h_{vw}^{(t+1)}} \times (d_{e_{vw}} + d_{x_v} + d_{x_w})}$$

is an input parameter (corresponding to the above second aggregation parameter).

In some embodiments, for improving the efficiency and accuracy of the message propagation, the above parameters such as $W_K$ and $W_S$ are shared during one round of propagation, that is, parameter sharing.

In certain embodiments of the present disclosure, the state information such as $h_{vw}^{(t+1)}$ on each edge during each round of message propagation in the chemical structure graph may be obtained in a manner of the message propagation on the edge to obtain the state information of the each edge after the plurality of rounds of message propagation.

For ease of implementing the message propagation and property prediction, in some embodiments, the each round of message propagation may represent a neural network layer, which may be referred to as a message propagation layer. For example, referring to FIG. 2d, input of the message propagation layer includes the node feature vector set X and the historical propagation state information such as $h_{vw}^{(t+1)}$ on all edges during the previous round of message propagation. For example, the input of the first round of message propagation layer may include the node feature vector set X and the state information $H^0$ on all the edges during the zeroth round of message propagation. After the neural network layer performs the message propagation, the state information $H^t$ on all the edges during the first round of message propagation is outputted.

$$H^0 = \{h_{vw}^{(0)}\}_{e_{vw} \in E} \text{ and } H^T = \{h_{vw}^{(T)}\}_{e_{vw} \in E}$$

respectively represent an input state vector set and an output state vector set of each edge.

Therefore, certain embodiments of the present disclosure provide a neural network including a plurality of message propagation layers to implement the message propagation and property prediction. Each message propagation layer implements one round of message propagation. For example, the message propagation may be implemented by using a multi-layer edge information propagation model based on the node information sharing. The multi-layer edge information propagation model is a neural network including a plurality of message propagation layers. By using the plurality of message propagation layers in the multi-layer edge information propagation model, the plurality of rounds of message propagation are performed on the edge according to the original node feature of the node and the original edge feature of the edge to obtain propagation state information of the edge after the plurality of rounds of message propagation.

Figure 2I:
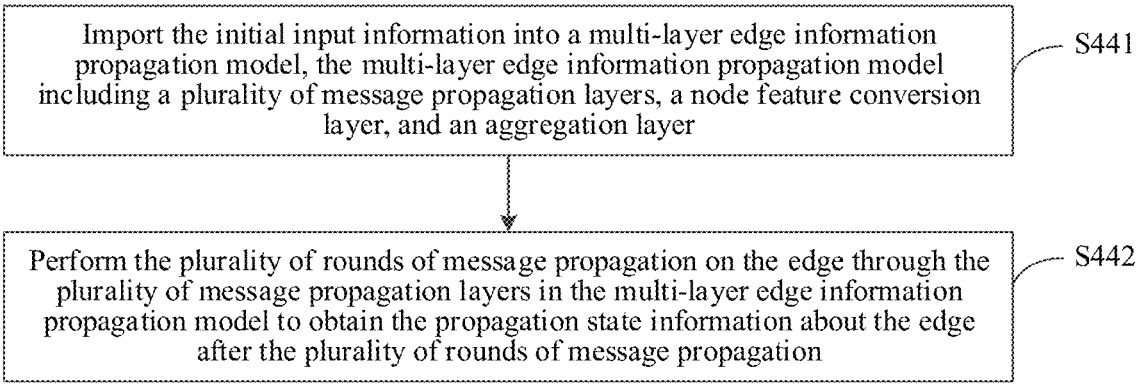

In some embodiments, as shown in FIG. 2i, step S42 may include the following:

S441. Import the initial input information into a multi-layer edge information propagation model, the multi-layer edge information propagation model including a plurality of message propagation layers, a node feature conversion layer, and an aggregation layer.

S442. Perform the plurality of rounds of message propagation on the edge through the plurality of message propagation layers in the multi-layer edge information propagation model to obtain the propagation state information of the edge after the plurality of rounds of message propagation.

For example, in some embodiments, a multi-layer edge information propagation model based on the node information sharing is provided. For a network structure thereof, refer to FIG. 2e. Referring to FIG. 2e, input of the model includes the feature vectors X of all nodes and the feature vectors E of all edges. First, initial state information $H^0$ on an edge is calculated according to the feature vectors X of all nodes and the feature vectors E of all edges. The initial state information is inputted to a first message propagation layer K1/S1 to perform message propagation, and the state information $H^1$ on all edges during or after the first round of message propagation is outputted. The feature vectors X of all nodes and the state information $H^1$ are inputted to a second message propagation layer K2/S2 to perform message propagation, and the state information $H^2$ on all edges during or after the second round of message propagation is outputted, and so on until the message propagation is performed on the $n^{th}$ message propagation layer Kn/Sn, and the state information $H^n$ on all edges during or after the $n^{th}$ round of message propagation is outputted.

205. Obtain a target feature of the edge according to the propagation state information.

The propagation state information such as $h_{vw}^{(t+1)}$ on each edge after the plurality of rounds of message propagation in the chemical structure graph may be obtained through the above steps. In certain embodiments of the present disclosure, a target feature of each edge, that is, a new feature of each edge, may be constructed according to the propagation state information of each edge after the plurality of rounds of message propagation. There are a plurality of specific construction manners. For example, current propagation state information of the edge may directly serve as the target feature of the edge. In some embodiments, when the state information is represented in a vector form, the current propagation state information of the edge may directly serve as the target feature vector of the edge, that is, a new feature vector of the edge.

206. Predict properties of the target compound according to the target feature of the edge, and output a property prediction result of the target compound.

Specifically, the property prediction result of the target compound may be obtained through classification. For example, the chemical structure graph is classified according to the target feature of the edge to obtain a classification result. A property prediction result of the target compound is obtained according to the classification result. For example, the classification result may directly serve as a property type of the target compound.

The types or property types of the chemical structure graph may be divided into chemical properties, biological properties, and the like. Specifically, the properties may include toxicity, solubility, carcinogenicity, and the like.

Figure 2J:
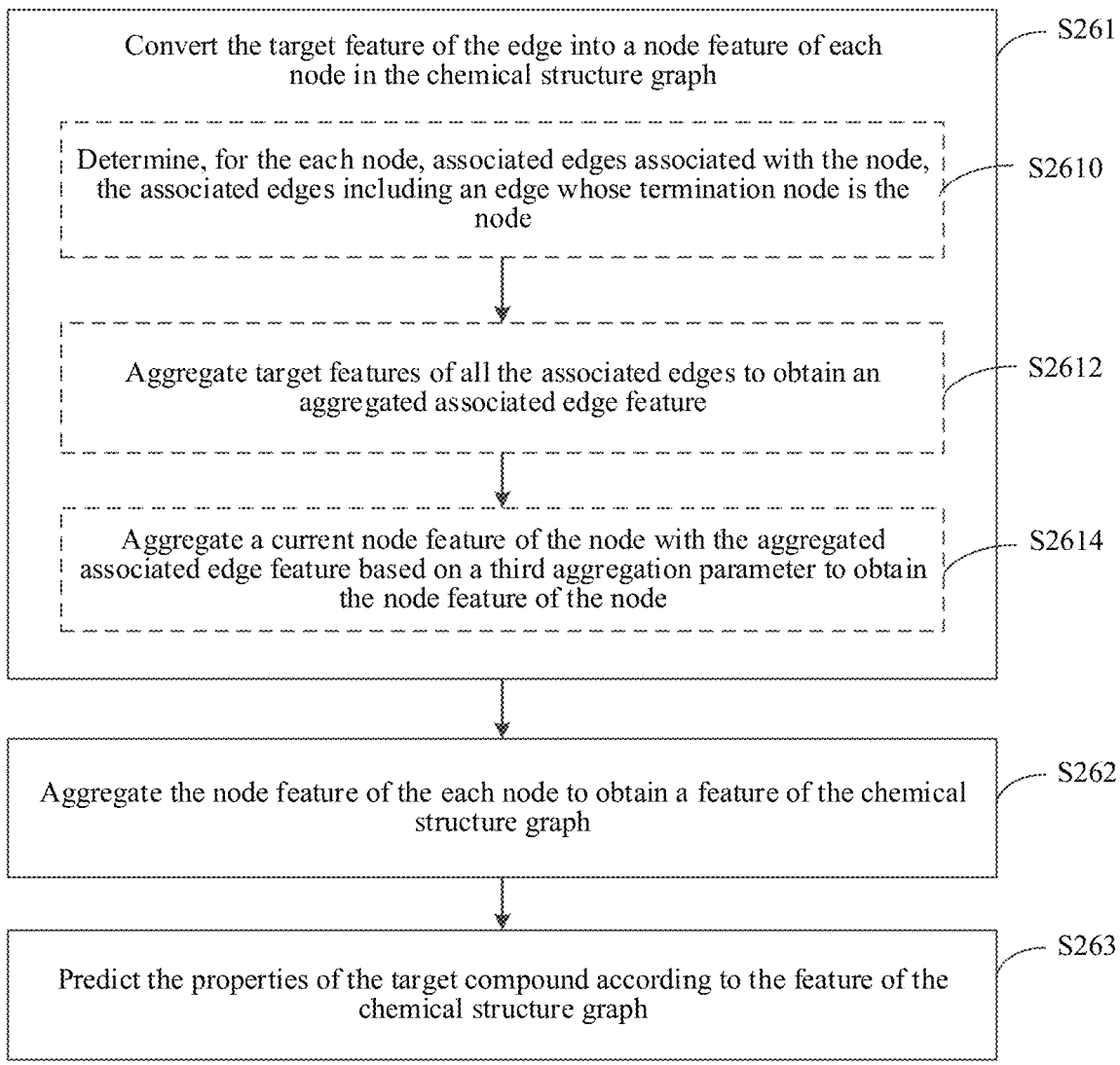

In some embodiments, for improving the accuracy of the property prediction, the feature of the edge may be converted into the feature of each node in the chemical structure graph. Then, the features of the nodes may be integrated into the feature of the chemical structure graph to perform the property prediction. Specifically, as shown in FIG. 2j, step 206 may include the following:

S261. Convert the target feature of the edge into a node feature of each node in the chemical structure graph.

S262. Aggregate the node feature of the each node to obtain a feature of the chemical structure graph.

S263. Predict the properties of the target compound according to the feature of the chemical structure graph.

There are a plurality of manners of converting the edge feature into the node feature. For example, for improving the accuracy of the property prediction or classification, in some embodiments, as shown in FIG. 2j, step S261 may include the following:

S2610. Determine, for the each node, associated edges associated with the node, the associated edges including an edge whose end node is the node.

S2612. Aggregate target features of all the associated edges to obtain an aggregated associated edge feature.

S2614. Aggregate a current node feature of the node with the aggregated associated edge feature based on a third aggregation parameter to obtain the node feature of the node.

The associated edges of each node may include an edge whose end node is the node. For example, the associated edges of the node v may include the neighboring edge, that is, the edge kv, whose end node is the node v, and the start node k of the associated edge is the neighboring node of the node v.

Figure 2K:
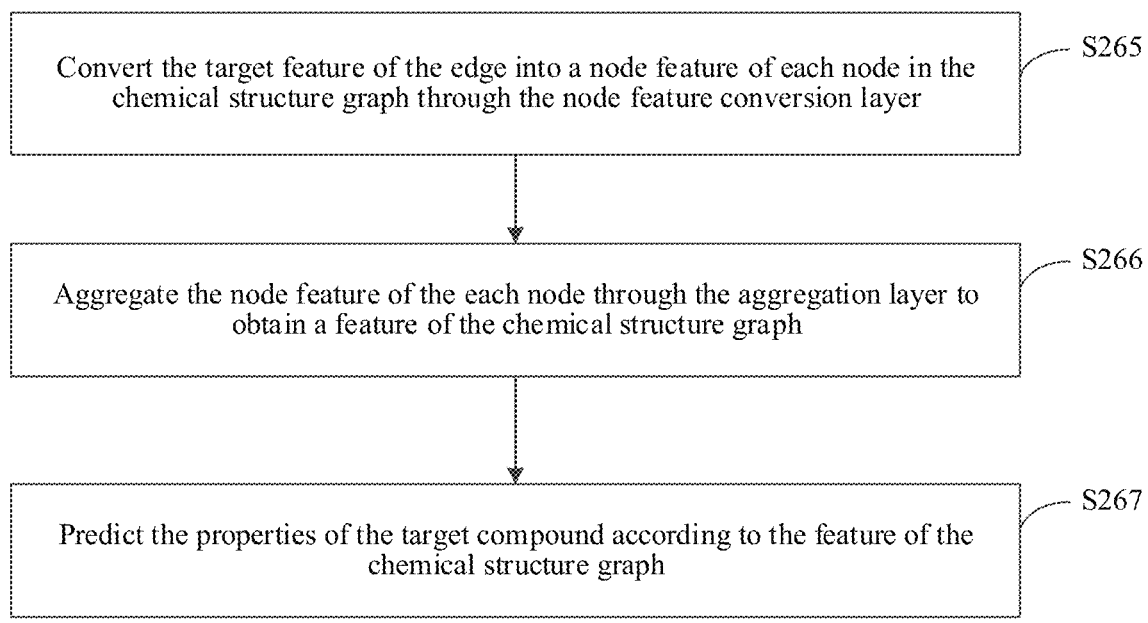
Figure 21:
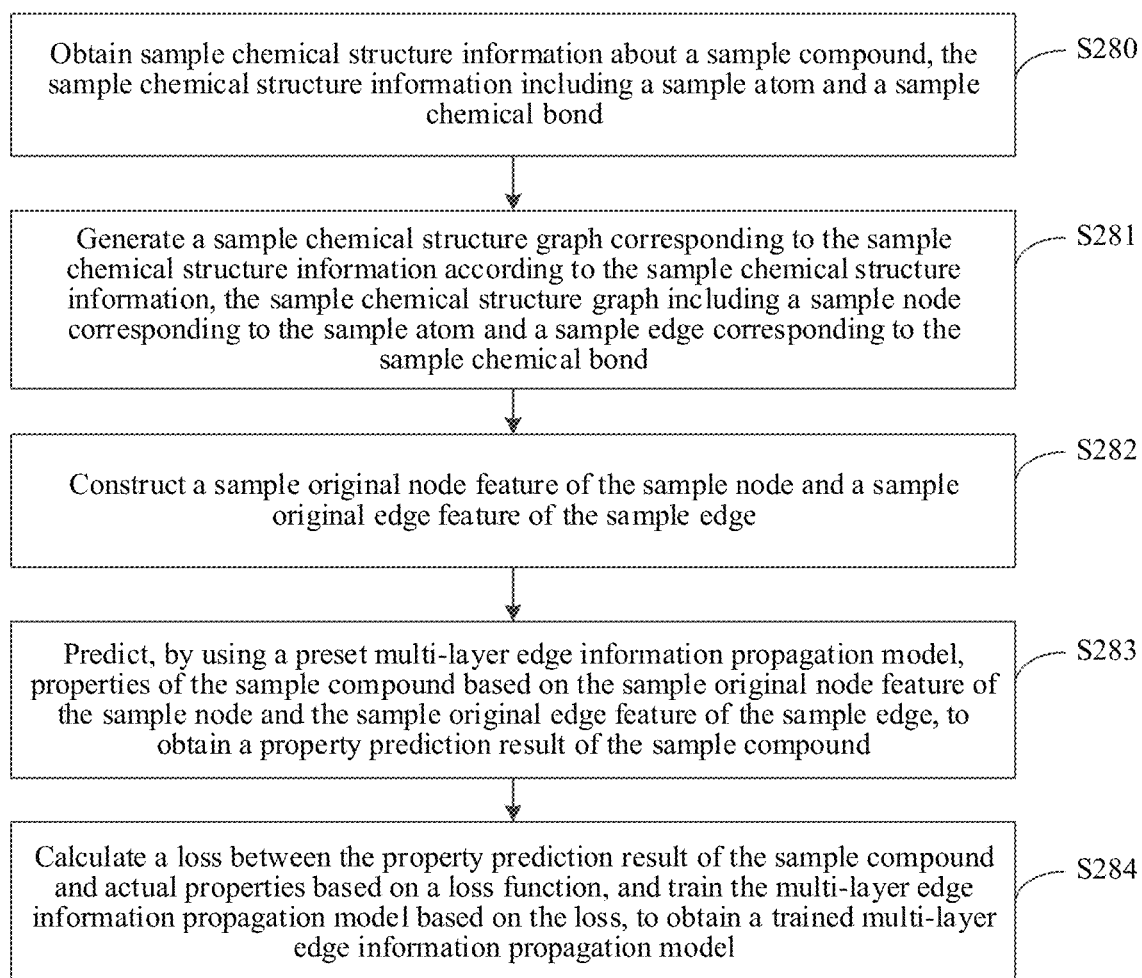

In some embodiments, the conversion and aggregation may be implemented by using the multi-layer edge information propagation model. Specifically, as shown in FIG. 2k, step 206 may include the following:

S265. Convert the target feature of the edge into a node feature of each node in the chemical structure graph through the node feature conversion layer.

S266. Aggregate the node feature of the each node through the aggregation layer to obtain a feature of the chemical structure graph.

S267. Predict the properties of the target compound according to the feature of the chemical structure graph.

For example, referring to FIG. 2e, the multi-layer edge information propagation model may further include a to node representation layer. The to node representation layer may convert the target feature vector of the edge into the feature vector of the node, that is, convert a vector representation of the edge into a vector representation of the node. Specifically, the input $H^n$ is given, and the vector representation of each node v may be calculated by using the following method:

$$h_v = \sigma\left(W_{out}\text{concat}\left(x_v, \sum_{k \in N(v)} h_{kv}^{(n)}\right)\right)$$

In the above formula, $$W_{out} \in R^{d_{h_v} \times \left(d_{x_v} + d_{h_{kv}^{(n)}}\right)}$$

represents an output parameter (corresponding to the third aggregation parameter), and $W_{out}$ is shared among all nodes. The feature vector representation of the edge is converted into the feature vector representation of the node through the to node representation.

In some embodiments, for facilitating calculation, the node feature of the each node may be aggregated to obtain the feature vector of a preset or fixed length, that is, the outputted node vector is converted into a graph representation vector of a fixed length.

For example, referring to FIG. 2e, the multi-layer edge information propagation model may further include the aggregation layer. The aggregation layer is mainly responsible for converting the feature vector of the node into the graph feature vector of the fixed length, that is, converting the outputted node vector into the graph representation vector of the fixed length. In some embodiments, for improving calculation efficiency, conversion is performed by using a sum function:

$$g = \sum_{v \in V} h_v$$

Through the above model, in certain embodiments of the present disclosure, a vector representation g of a fixed length of any graph may be obtained.

In addition to the sum function for implementing aggregation, aggregation implementations of the aggregation layer may further include max pooling, self-attention, and the like.

Feature information such as the feature vector on the chemical structure graph of the target compound may be obtained in the above manner. Then, properties are predicted based on the feature information of the graph. For example, in some embodiments, property classification may be performed on the chemical structure graph according to the feature information of the chemical structure graph to obtain the property prediction result of the target compound. The types of the chemical structure graph may include the biological properties, chemical properties, and the like, for example, toxicity, solubility, and carcinogenicity.

For example, in some embodiments, the graph may be classified according to the feature information of the chemical structure graph through a classifier such as a multi-layer perception classifier. Specifically, the feature information of the chemical structure graph is inputted to the multi-layer perception classifier, and the property classification is performed on the graph of the target compound according to the feature information through the classifier, to obtain the property classification result.

In certain embodiments of the present disclosure, the multi-layer edge information propagation model may be a model after sample training. As shown in FIG. 2l, a training process thereof may include the following:

S280. Obtain sample chemical structure information of a sample compound, the sample chemical structure information including a sample atom and a sample chemical bond.

S281. Generate a sample chemical structure graph corresponding to the sample chemical structure information according to the sample chemical structure information, the sample chemical structure graph including a sample node corresponding to the sample atom and a sample edge corresponding to the sample chemical bond.

S282. Construct a sample original node feature of the sample node and a sample original edge feature of the sample edge.

S283. Predict, by using a preset multi-layer edge information propagation model, properties of the sample compound based on the sample original node feature of the sample node and the sample original edge feature of the sample edge, to obtain a property prediction result of the sample compound. Specifically, for the property prediction result of the sample compound, refer to the description of the above embodiments.

S284. Calculate a loss between the property prediction result of the sample compound and actual properties based on a loss function, and train the multi-layer edge information propagation model based on the loss, to obtain a trained multi-layer edge information propagation model.

There are a plurality of application scenarios of the property prediction method provided in certain embodiments of the present disclosure. For example, properties of a medicine are classified in a pharmaceutical analysis scenario. In another example, similar functions are searched for in scenarios such as software engineering and vulnerability.

It can be learned from the above that, in certain embodiments of the present disclosure, chemical structure information of a target compound is obtained, where the chemical structure information includes an atom and a chemical bond; a chemical structure graph corresponding to the chemical structure information is generated according to the chemical structure information, where the chemical structure graph includes a node corresponding to the atom and an edge corresponding to the chemical bond; an original node feature of the node and an original edge feature of the edge are constructed; a plurality of rounds of message propagation are performed on the edge according to the original node feature of the node and the original edge feature of the edge to obtain propagation state information of the edge after the plurality of rounds of message propagation; a target feature of the edge is obtained according to the current propagation state information; and properties of the target compound are predicted according to the target feature of the edge, and a property prediction result of the target compound is outputted. In this solution, the chemical structural formula of the target compound may be converted into the data structure such as the graph, the feature of the edge corresponding to the chemical bond in the graph is obtained in the manner based on a plurality of times of message propagation on the graph data (that is, the feature information of the chemical bond in the target compound is obtained), and the properties of the target compound are predicted based on the feature of the edge. Since the chemical structural formula of any substance may be converted into the graph data structure, this solution may be applicable to any neural network and be better applicable to the neural network with relatively high flexibility and universality, and may improve the stability and effect of the property prediction, to further improve the accuracy of the property prediction.

In addition, because properties of the compound are often related to the existing chemical bond, and the essence of many chemical reactions is actually breaking and recombination of the chemical bond, the properties of the target compound may be accurately predicted based on the feature information of the chemical bond, greatly improving the accuracy of the property prediction.

According to the method described in the foregoing embodiments, the following further performs detailed description by using examples.

In this embodiment, the compound property prediction apparatus specifically integrated in the computing device is used as an example for description.

1. The model is trained.

First, the computing device may obtain a sample compound set, and the multi-layer edge information propagation model based on the node information sharing is trained according to the sample compound set. Referring to FIG. 2e, the multi-layer edge information propagation model may include a plurality of message propagation layers, a to node representation layer, and an aggregation layer. For the structure of the model, refer to the description of the above embodiments.

In certain embodiments of the present disclosure, the multi-layer edge information propagation model may be trained based on the sample chemical structure information (such as chemical structural formula) of the sample compound marked with properties, for example, trained in a manner of back propagation. Specifically, the training manner is as follows:

(1). The computing device obtains a sample chemical structural formula of the sample compound, the sample chemical structural formula including a sample atom and a sample chemical bond.

(2). The computing device converts the sample chemical structural formula into a sample chemical structure graph, the sample chemical structure graph including a sample node corresponding to the sample atom and a sample edge corresponding to the sample chemical bond.

Specifically, for the conversion manner, refer to the description of the above embodiments.

(3). The computing device performs, by using the multi-layer edge information propagation model, the plurality of rounds of message propagation on the sample edge according to the sample original node feature of the sample node and the sample original edge feature of the sample edge, to obtain sample propagation state information of the sample edge after the plurality of rounds of message propagation.

Specifically, for the message propagation manner, refer to the message propagation manner introduced above.

(4). The computing device obtains, by using the multi-layer edge information propagation model, a sample target feature of the sample edge based on the sample propagation state information.

(5). The computing device predicts, by using the classifier, properties of the sample compound according to the sample target feature of the sample edge, and outputs a property prediction result of the sample compound.

Specifically, for the predicting properties of the sample compound according to the sample target feature, refer to the above process of predicting the target compound based on the target feature of the edge.

(6). The computing device calculates a loss between the property prediction result of the sample compound and marked properties based on a loss function, and trains the multi-layer edge information propagation model based on the loss, to obtain a trained multi-layer edge information propagation model.

For example, a cross entropy loss function may be used for measuring a difference between the current model prediction and an actual mark y. The loss function is as follows:

$$o_i = MLP(g_i)$$

$$loss(y_i, o_i) = CrossEntropy(y_i, o_i)$$

In some embodiments, the final loss function may vary with specific tasks. For example, if the last task is a regression task, the loss function may be a mean-square error (MSE) loss function.

2. Properties of the target compound may be predicted through the trained multi-layer edge information propagation model.

Figure 3:
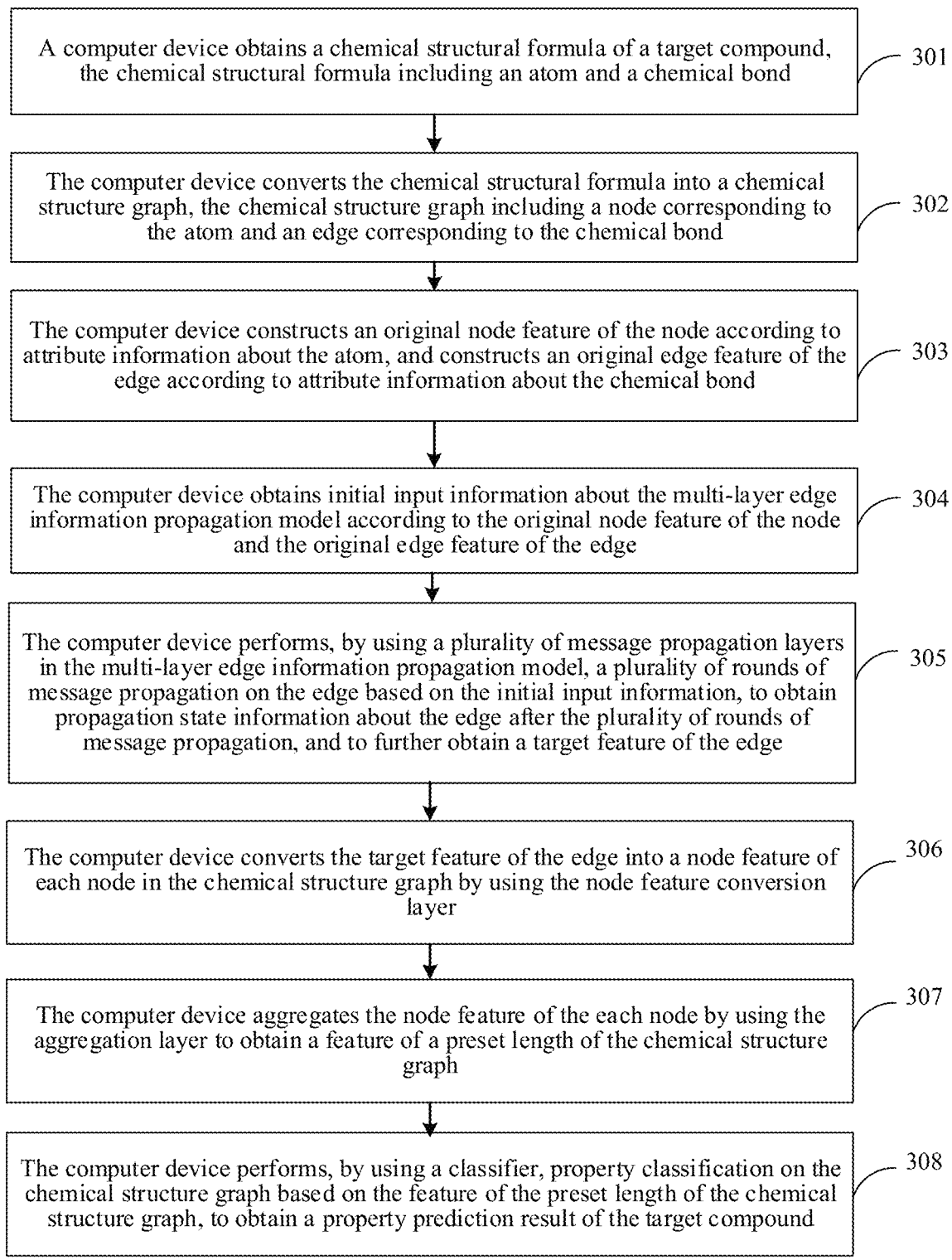
FIG. 3 is another schematic flowchart of a compound property prediction method according to one or more embodiments of the present disclosure.

As shown in FIG. 3, a specific process of a compound property prediction method is as follows:

301. A computing device obtains a chemical structural formula of a target compound, the chemical structural formula including an atom and a chemical bond.

For example, the computing device may obtain the chemical structural formula of a medicine.

302. The computing device converts the chemical structural formula into a chemical structure graph, the chemical structure graph including a node corresponding to the atom and an edge corresponding to the chemical bond.

303. The computing device constructs an original node feature of the node according to attribute information of the atom, and constructs an original edge feature of the edge according to attribute information of the chemical bond.

For example, a charge number, a proton number, a neutron number, or the like of the atom is modeled into a feature vector of the atom, and a chemical bond type, a chemical bond valence state, or the like is modeled into a feature vector of the edge corresponding to the chemical bond.

304. The computing device obtains initial input information of the multi-layer edge information propagation model according to the original node feature of the node and the original edge feature of the edge.

For example, the initial input information is obtained through calculation by using the following formula:

$$h_{vw}^{(0)} = \sigma(W_{in} \text{concat}(e_{vw}, x_v, x_w)), \text{ where}$$

$$W_{in} \in R^{d_{h_{vw}^{(l+1)}} \times (d_{e_{vw}} + d_{x_v} + d_{x_w})}$$

represents an aggregation parameter or an input parameter.

305. The computing device performs, by using a plurality of message propagation layers in the multi-layer edge information propagation model, a plurality of rounds of message propagation on the edge based on the initial input information, to obtain propagation state information of the edge after the plurality of rounds of message propagation, and to further obtain a target feature of the edge.

For details, refer to the above process of message propagation. For example, referring to FIG. 2e, input of the model includes the feature vectors X of all nodes and the feature vectors E of all edges. First, initial state information $H^0$ of the edge is calculated according to the feature vectors X of all nodes and the feature vectors E of all edges. The initial state information is inputted to a first message propagation layer K1/S1 to perform message propagation, and the state information $H^1$ on all edges during or after the first round of message propagation is outputted. The feature vectors X of all nodes and the state information $H^1$ are inputted to a second message propagation layer K2/S2 to perform message propagation, and the state information $H^2$ on all edges during or after the second round of message propagation is outputted, and so on until the message propagation is performed on the $n^{th}$ message propagation layer Kn/Sn, and the state information $H^n$ on all edges during or after the $n^{th}$ round of message propagation is outputted.

306. The computing device converts the target feature of the edge into a node feature of each node in the chemical structure graph through the node feature conversion layer.

For example, referring to FIG. 2e, the input $H^n$ is given, and the vector representation of each node v may be calculated by using the following method:

$$h_v = \sigma\left(W_{out}\text{concat}\left(x_v, \sum_{k\in N(v)} h_{kv}^{(n)}\right)\right)$$

In the above formula, $$W_{out} \in R^{d_{h_v} \times \left(d_{x_v} + d_{h_{kv}^{(n)}}\right)}$$

represents an output parameter (corresponding to the third aggregation parameter), and $W_{out}$ is shared among all nodes. The feature vector representation of the edge is converted into the feature vector representation of the node through the to node representation.

307. The computing device aggregates the node feature of the each node by using the aggregation layer to obtain a feature of a preset length of the chemical structure graph.

For example, referring to FIG. 2e, the aggregation layer uses the sum function to perform conversion:

$$g = \sum_{v \in V} h_v$$

Through the above model, in an embodiment of present disclosure, a vector representation g of a fixed length of any chemical structure graph may be obtained.

308. The computing device performs, by using a classifier, property classification on the chemical structure graph based on the feature of the preset length of the chemical structure graph, to obtain a property prediction result of the target compound.

For example, the chemical structure graph may be classified according to the feature information of the chemical structure graph through a multi-layer perception classifier. Specifically, the feature information of the chemical structure graph is inputted to the multi-layer perception classifier, and the property classification is performed on the chemical structure graph of the target compound according to the feature information through the classifier, to obtain the property classification result such as toxicity, solubility, or carcinogenicity.

For example, in the manner introduced above, the chemical structural formula of the medicine may be converted into the structure of the chemical structure graph, the feature vector of the chemical structure graph is obtained through the message propagation, the property classification is performed on the chemical structure graph based on the feature vector of the chemical structure graph, and the classification result such as the toxicity is obtained. In this case, the property prediction result of the medicine is the toxicity.

It can be learned from the above that, in certain embodiments of the present disclosure, the given compound is converting into a representation form of the graph, and then properties of the compound are modeled by using the multi-layer edge information propagation model based on the node information sharing, to determine the properties corresponding to any inputted compound, and improve the accuracy and stability of the property prediction.

To implement the above method better, certain embodiments of the present disclosure further provide a compound property prediction apparatus. The compound property prediction apparatus may be integrated in a computing device such as a server, a terminal, or another device.

Figure 4A:
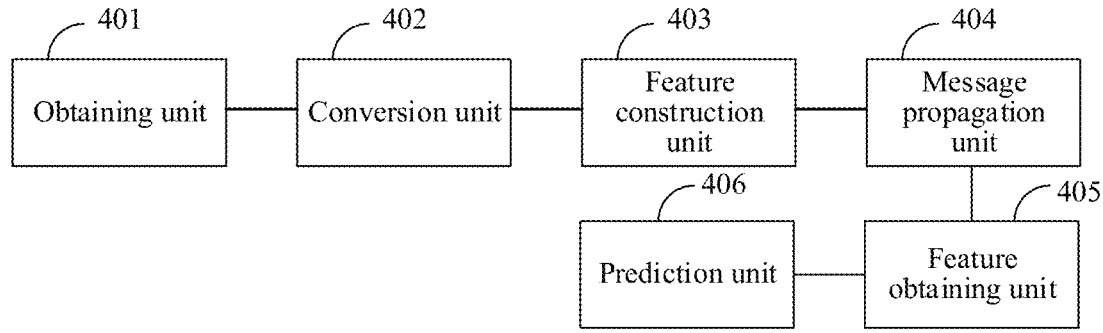
FIG. 4a is a schematic structural diagram of a compound property prediction apparatus according to one or more embodiments of the present disclosure.

The compound property prediction apparatus may include a number of units and/or modules, where each of the units or modules may be a structural component and/or a functional component of the compound property prediction apparatus, and any one of the units or modules may be detachable from the compound property prediction apparatus. The units or modules may be implemented using software, and can be developed using a computer programming language and using hardware such as a processor and/or memory. For example, as shown in FIG. 4a, the compound property prediction apparatus may include an obtaining unit 401, a conversion unit 402, a feature construction unit 403, a message propagation unit 404, a feature obtaining unit 405, and a prediction unit 406 as follows:

The obtaining unit 401 is configured to obtain chemical structure information of a target compound, the chemical structure information including an atom and a chemical bond.

The conversion unit 402 is configured to generate a chemical structure graph corresponding to the chemical structure information according to the chemical structure information, the chemical structure graph including a node corresponding to the atom and an edge corresponding to the chemical bond.

The feature construction unit 403 is configured to construct an original node feature of the node and an original edge feature of the edge.

The message propagation unit 404 is configured to perform a plurality of rounds of message propagation on the edge according to the original node feature of the node and the original edge feature of the edge to obtain propagation state information of the edge after the plurality of rounds of message propagation.

The feature obtaining unit 405 is configured to obtain a target feature of the edge according to the propagation state information.

The prediction unit 406 is configured to predict properties of the target compound according to the target feature of the edge, and output a property prediction result of the target compound.

Figure 4B:
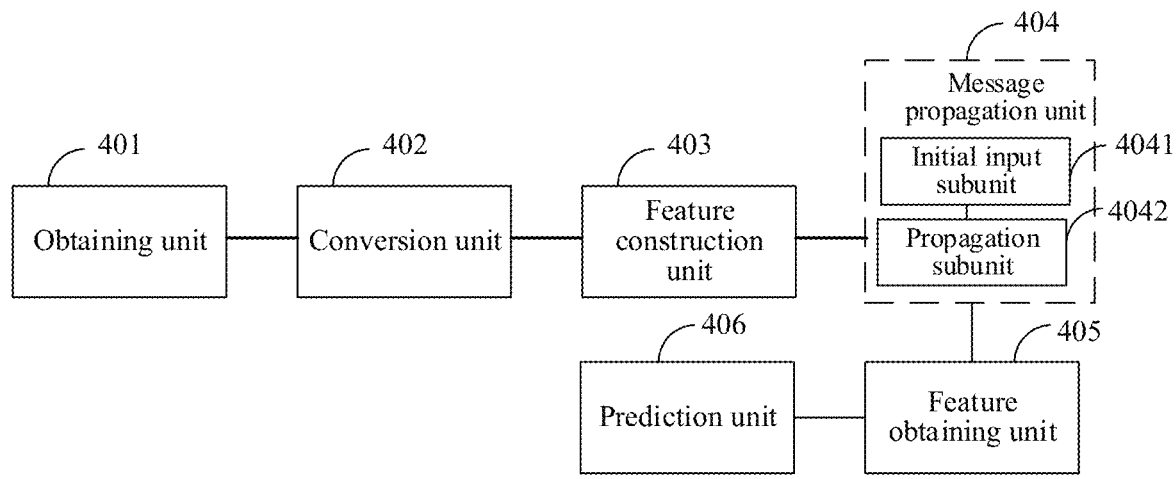
FIG. 4b is another schematic structural diagram of a compound property prediction apparatus according to one or more embodiments of the present disclosure.

In some embodiments, referring to FIG. 4b, the message propagation unit 404 may include: an initial input subunit 4041, configured to obtain initial input information of the plurality of rounds of message propagation according to the original node feature of the node and the original edge feature of the edge; and a propagation subunit 4042, configured to perform the plurality of rounds of message propagation on the edge based on the initial input information to obtain the propagation state information of the edge after the plurality of rounds of message propagation.

In some embodiments, the propagation subunit 4042 is configured to use the initial input information as current input of a current round of message propagation, and perform the current round of message propagation based on the current input; obtain current propagation state information of the edge during the current round of message propagation according to the original node feature of the node, a current edge feature of the edge, and historical propagation state information, the historical propagation state information being propagation state information of the edge during a historical round of message propagation; and update the current input according to the current propagation state information and the original node feature of the node at the time of entering a next round of message propagation, and return to perform the operation of performing the current round of message propagation based on the current input until all rounds of message propagation are completed, to obtain the propagation state information of the edge after the plurality of rounds of message propagation.

In some embodiments, the propagation subunit 4042 is configured to: determine all in-edges corresponding to a start node of the edge; aggregate, for each in-edge, a current edge feature of the in-edge and an original node feature of a node on the in-edge with historical propagation state information of the in-edge during the historical round of message propagation to obtain information of the in-edge; integrate information of all the in-edges to obtain message information of the edge during the current round of message propagation; and aggregate the historical propagation state information of the edge during the historical round of message propagation with the message information to obtain the current propagation state information of the edge during the current round of message propagation.

In some embodiments, the propagation subunit 4042 is configured to: aggregate a current edge feature of the in-edge and an original node feature of a node on the in-edge with historical propagation state information of the in-edge during the historical round of message propagation according to a message generation function to obtain an aggregated feature; and process the aggregated feature based on a first activation function to obtain the information of the in-edge.

In some embodiments, the propagation subunit 4042 is configured to: obtain referential historical propagation state information of the edge during referential historical round of message propagation; aggregate the referential historical propagation state information with the message information according to a first aggregation parameter to obtain aggregated propagation state information; and process the aggregated propagation state information based on a second activation function to obtain the current propagation state information of the edge during the current round of message propagation.

In some embodiments, the propagation subunit 4042 is configured to: aggregate the original edge feature of the edge with the original node feature of the node on the edge according to a second aggregation parameter to obtain an aggregated edge feature of the edge; and process the aggregated edge feature based on a third activation function to obtain the referential historical propagation state information of the edge during the referential historical round of message propagation.

Figure 4C:
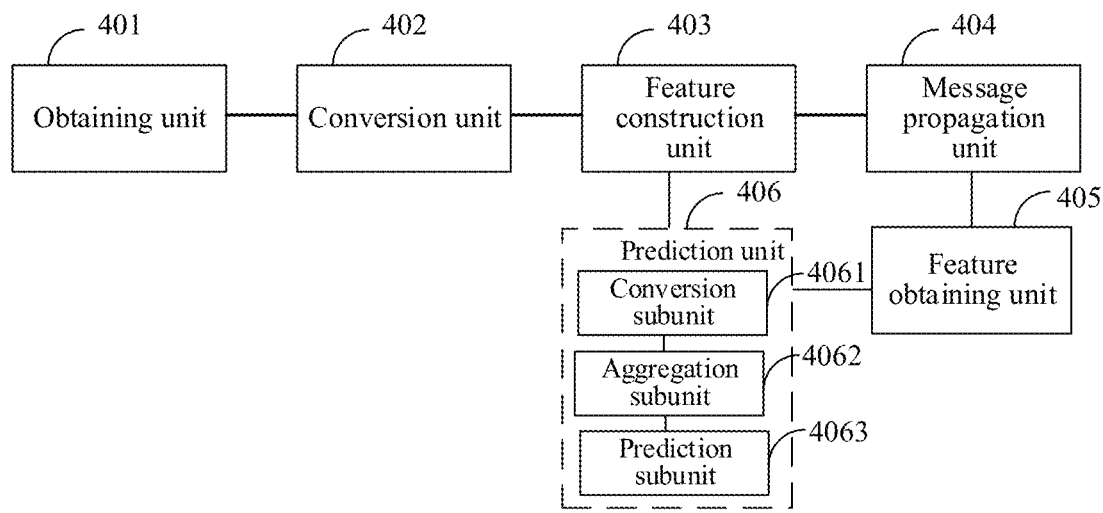
FIG. 4c is still another schematic structural diagram of a compound property prediction apparatus according to one or more embodiments of the present disclosure.

In some embodiments, referring to FIG. 4c, the prediction unit 406 may include: a conversion subunit 4061, configured to convert the target feature of the edge into a node feature of each node in the chemical structure graph; an aggregation subunit 4062, configured to aggregate the node feature of the each node to obtain a feature of the chemical structure graph; and a prediction subunit 4063, configured to predict the properties of the target compound according to the feature of the chemical structure graph.

In some embodiments, the conversion subunit 4061 is configured to: determine, for the each node, associated edges associated with the node, the associated edges including an edge whose end node is the node; aggregate target features of all the associated edges to obtain an aggregated associated edge feature; and aggregate a current node feature of the node with the aggregated associated edge feature based on a third aggregation parameter to obtain the node feature of the node.

In some embodiments, the feature construction unit 403 is configured to: construct the original node feature of the node according to attribute information of the atom; and construct the original edge feature of the edge according to attribute information of the chemical bond.

In some embodiments, the propagation subunit 4042 is configured to: import the initial input information into a multi-layer edge information propagation model, the multi-layer edge information propagation model including a plurality of message propagation layers, a node feature conversion layer, and an aggregation layer; and perform the plurality of rounds of message propagation on the edge through the plurality of message propagation layers in the multi-layer edge information propagation model to obtain the propagation state information of the edge after the plurality of rounds of message propagation.

The prediction unit 406 is configured to: convert the target feature of the edge into a node feature of each node in the chemical structure graph through the node feature conversion layer; aggregate the node feature of the each node through the aggregation layer to obtain a feature of the chemical structure graph; and predict the properties of the target compound according to the feature of the chemical structure graph.

Figure 4D:
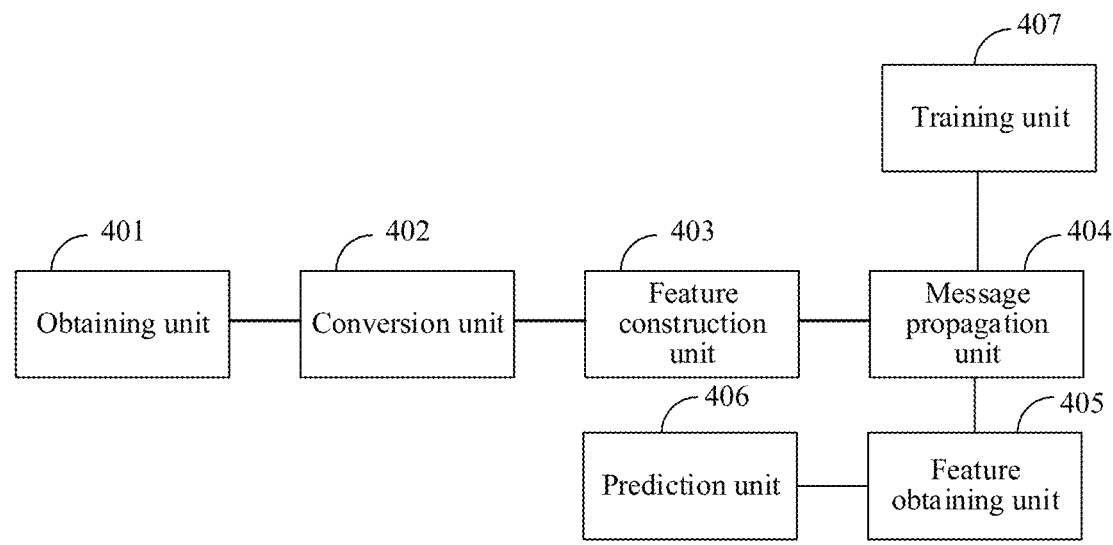
FIG. 4d is yet another schematic structural diagram of a compound property prediction apparatus according to one or more embodiments of the present disclosure.

In some embodiments, referring to FIG. 4d, the compound property prediction apparatus further includes a training unit 407. The training unit 407 may be specifically configured to: obtain sample chemical structure information of a sample compound, the sample chemical structure information including a sample atom and a sample chemical bond; generate a sample chemical structure graph corresponding to the sample chemical structure information according to the sample chemical structure information, the sample chemical structure graph including a sample node corresponding to the sample atom and a sample edge corresponding to the sample chemical bond; construct a sample original node feature of the sample node and a sample original edge feature of the sample edge; predict, by using a preset multi-layer edge information propagation model, properties of the sample compound based on the sample original node feature of the sample node and the sample original edge feature of the sample edge, to obtain a property prediction result of the sample compound; and calculate a loss between the property prediction result of the sample compound and actual properties based on a loss function, and train the multi-layer edge information propagation model based on the loss, to obtain a trained multi-layer edge information propagation model.

During specific implementation, the above units may be implemented as independent entities, or may be randomly combined, or may be implemented as a same entity or several entities. For specific implementation of the above units, refer to the foregoing method embodiments. Details are not described herein again.

It can be learned from the above that, according to the compound property prediction apparatus in certain embodiments of the present disclosure, the obtaining unit 401 obtains chemical structure information of a target compound, where the chemical structure information includes an atom and a chemical bond; the conversion unit 402 generates a chemical structure graph corresponding to the chemical structure information according to the chemical structure information, where the chemical structure graph includes a node corresponding to the atom and an edge corresponding to the chemical bond; the feature construction unit 403 constructs an original node feature of the node and an original edge feature of the edge; the message propagation unit 404 performs a plurality of rounds of message propagation on the edge according to the original node feature of the node and the original edge feature of the edge to obtain propagation state information of the edge after the plurality of rounds of message propagation; the feature obtaining unit 405 obtains a target feature of the edge according to the propagation state information; and the prediction unit 406 predicts properties of the target compound according to the target feature of the edge and outputs a property prediction result of the target compound. In this solution, a chemical structural formula of a target compound may be converted into a data structure such as a graph, the feature of the edge corresponding to the chemical bond in the graph is obtained in a manner based on a plurality of times of message propagation on graph data, and the properties of the target compound are predicted based on the feature of the edge. Therefore, the properties of the target compound can be accurately predicted, greatly improving the accuracy of the property prediction.

Figure 5:
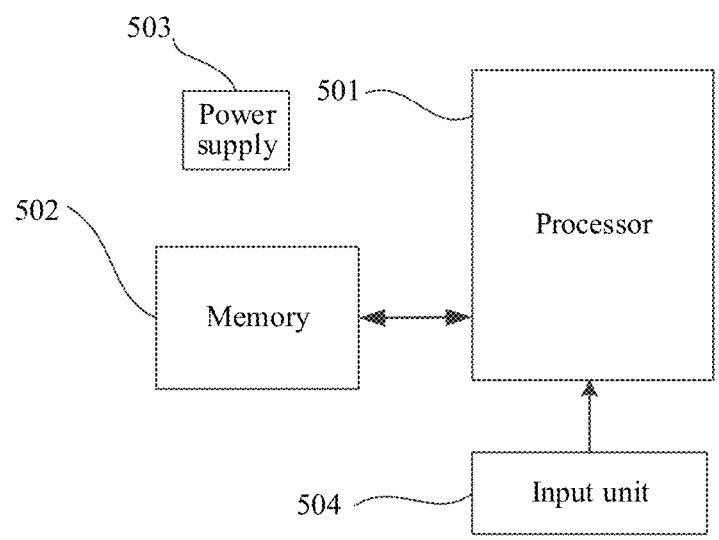
FIG. 5 is a schematic structural diagram of a computer device according to one or more embodiments of the present disclosure.

Certain embodiments of the present disclosure further provide a computing device. FIG. 5 is a schematic structural diagram of a computing device according to certain embodiments of the present disclosure. Specifically:

The computing device may include components such as a processor 501 of one or more processing cores, a memory 502 of one or more computer-readable storage media, a power supply 503, and an input unit 504. A person of skill in the art can understand that, a structure of the computing device shown in FIG. 5 does not constitute a limit on the computing device, and may include components that are more or fewer than those shown in the figure, or a combination of some components, or different component arrangements.

The processor 501 is a control center of the computing device, and connects to various parts of the entire computing device by using various interfaces and lines. By running or executing software programs and/or modules stored in the memory 502, and invoking data stored in the memory 502, the processor performs various functions and data processing of the computing device, thereby performing overall monitoring on the computing device. Optionally, the processor 501 may include one or more processing cores. In some embodiments, the processor 501 may integrate an application processor and a modem processor. The application processor mainly processes an operating system, a user interface, an application program, and the like. The modem processor mainly processes wireless communication. It may be understood that the above modem processor may alternatively not be integrated into the processor 501.

The memory 502 may be configured to store a software program and a module, and the processor 501 runs the software program and the module that are stored in the memory 502, to implement various functional applications and data processing. The memory 502 may mainly include a program storage area and a data storage area. The program storage area may store an operating system, an application program required by at least one function (such as a sound playing function and an image display function), and the like. The data storage area may store data created according to use of the computing device, and the like. In addition, the memory 502 may include a high speed random access memory, and may also include a non-volatile memory, such as at least one magnetic disk storage device, a flash memory, or another volatile solid-state storage device. Correspondingly, the memory 502 may further include a memory controller, so that the processor 501 can access the memory 502.

The computing device further includes the power supply 503 for supplying power to the components. In some embodiments, the power supply 503 may be logically connected to the processor 501 by using a power supply management system, thereby implementing functions, such as charging, discharging, and power consumption management, by using the power supply management system. The power supply 503 may further include one or more of a direct current or alternating current power supply, a recharging system, a power failure detection circuit, a power supply converter or inverter, a power supply state indicator, and any other components.

The computing device may further include the input unit 504. The input unit 504 may be configured to receive entered numeric or character information and generate keyboard, mouse, joystick, optical, or trackball signal input related to user settings and function control.

Although not shown in the figure, the computing device may further include a display unit, and the like. Details are not described herein again. Specifically, in this embodiment, the processor 501 of the computing device may load, according to the following instructions, executable files corresponding to processes of one or more application programs into the memory 502. The processor 501 runs the application programs stored in the memory 502, to implement various functions:

Chemical structure information of a target compound is obtained, where the chemical structure information includes an atom and a chemical bond; a chemical structure graph corresponding to the chemical structure information is generated according to the chemical structure information, where the chemical structure graph includes a node corresponding to the atom and an edge corresponding to the chemical bond; an original node feature of the node and an original edge feature of the edge are constructed; a plurality of rounds of message propagation are performed on the edge according to the original node feature of the node and the original edge feature of the edge to obtain propagation state information of the edge after the plurality of rounds of message propagation; a target feature of the edge is obtained according to the propagation state information; and properties of the target compound are predicted according to the target feature of the edge, and a property prediction result of the target compound is outputted; or chemical structure information of a target compound is obtained, where the chemical structure information includes an atom and a chemical bond; a chemical structure graph corresponding to the chemical structure information is generated according to the chemical structure information, where the chemical structure graph includes a node corresponding to the atom and an edge corresponding to the chemical bond; initial input information of the multi-layer edge information propagation model is obtained according to an original node feature vector of the node and an original edge feature vector of the edge; a plurality of rounds of message propagation are performed on the edge based on the initial input information by using the multi-layer edge information propagation model, to obtain propagation state information of the edge after the plurality of rounds of message propagation; a target feature of the edge is obtained based on the propagation state information by using the multi-layer edge information propagation model; and properties of the target compound are predicted according to the target feature of the edge by using the multi-layer edge information propagation model, and a property prediction result of the target compound is outputted.

Refer to the foregoing embodiments for details of the above operations, and details are not described herein again.

It can be learned from the above that, in certain embodiments of the present disclosure, after obtaining the chemical structure information of the target compound, the computing device generates a chemical structure graph corresponding to the chemical structure information according to the chemical structure information, where the chemical structure graph includes a node corresponding to the atom and an edge corresponding to the chemical bond; constructs an original node feature of the node and an original edge feature of the edge; performs a plurality of rounds of message propagation on the edge according to the original node feature of the node and the original edge feature of the edge to obtain propagation state information of the edge after the plurality of rounds of message propagation; obtains a target feature of the edge according to the propagation state information; and predicts properties of the target compound according to the target feature of the edge, and outputs a property prediction result of the target compound. In this solution, a chemical structural formula of a target compound may be converted into a data structure such as a graph, the feature of the edge corresponding to the chemical bond in the graph is obtained in a manner based on a plurality of times of message propagation on graph data, and the properties of the target compound are predicted based on the feature of the edge. Therefore, the properties of the target compound can be accurately predicted, greatly improving the accuracy of the property prediction.

In some embodiments, the above computing device in which the compound property prediction apparatus is integrated may be a node in a data sharing system (such as a blockchain system), that is, the compound property prediction method provided in certain embodiments of the present disclosure may be implemented by the node in the data sharing system (such as the blockchain system). In some embodiments, the property prediction result may be further stored in the data sharing system.

One or more nodes in the data sharing system may receive input information during normal working, and maintain data in the data sharing system based on the received input information. To ensure information interoperability in the data sharing system, there may be an information connection between any two nodes in the data sharing system, and information transmission may be performed between the nodes through the above information connection. For example, when any node in the data sharing system receives input information, other nodes in the data sharing system obtain the input information according to a consensus algorithm, and store the input information as shared data, so that data stored on all nodes in the data sharing system is consistent.

Each node in the data sharing system has a node identifier corresponding to the node, and each node in the data sharing system may store a node identifier of another node in the data sharing system, to broadcast a generated block to the another node in the data sharing system according to the node identifier of the another node subsequently. Each node may maintain a node identifier list shown in the following table, and correspondingly store a node name and a node identifier into the node identifier list. A node identifier may be an Internet Protocol (IP) address and any other information that can be used to identify a node. For example, when a terminal or server in which a video identification apparatus is integrated performs video abnormality identification on a video to be identified, and obtains an identification result, the terminal or server broadcasts the identification result to a network device in the data sharing system corresponding to a node identifier in the node identifier list. Only an IP address in the following table is used as an example for description.

| Node name | Node identifier |
|---|---|
| Node 1 | 117.114.151.174 |
| Node 2 | 117.116.189.145 |
| ... | ... |
| Node N | 119.123.789.258 |

Figure 6B:
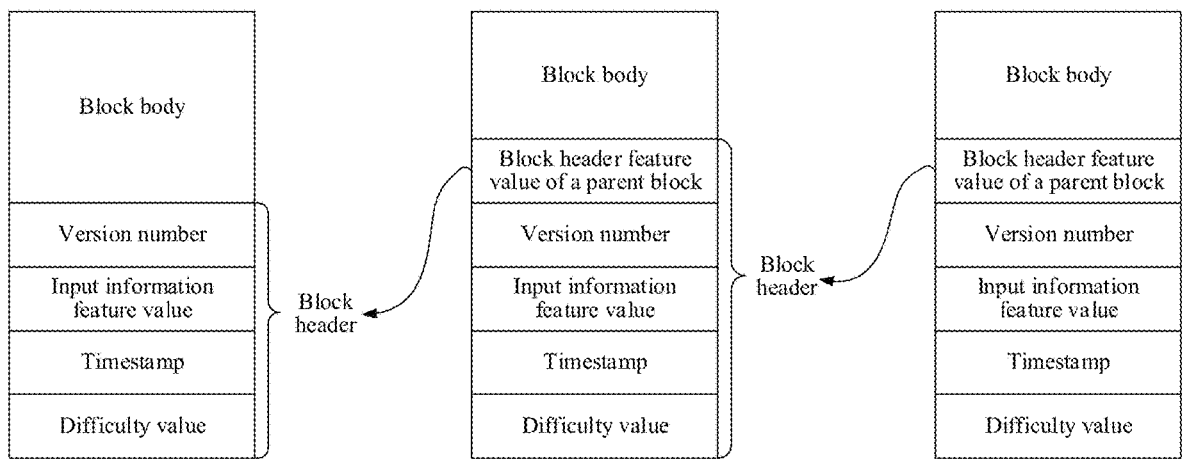

One blockchain is stored in each node in the data sharing system, and the blockchains in the nodes are all the same. The blockchain includes a plurality of blocks. Referring to FIG. 6b, the blockchain includes a plurality of blocks. A genesis block includes a block header and a block body. The block header stores an input information feature value, a version number, a timestamp, and a difficulty value. The block body stores input information. A next block of the genesis block takes the genesis block as a parent block, the next block also includes a block header and a block body, and the block header stores an input information feature value of the current block, a block header feature value of the parent block, a version number, a timestamp, and a difficulty value. The rest is deduced by analogy, so that block data stored in each block in the blockchain is associated with block data stored in a parent block, thereby ensuring security of input information in the block. In this embodiment, the identification result may be stored in the block body.

Figure 6C:
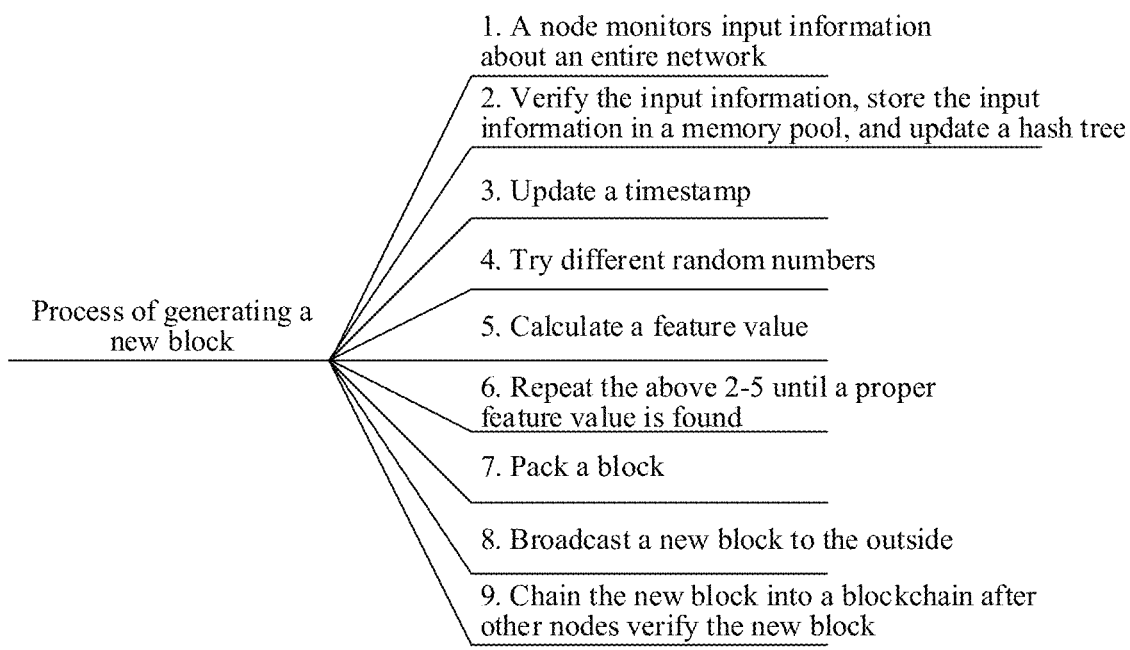
FIG. 6c is a schematic flowchart of block generation in the blockchain shown in FIG. 6b.

When each block in the blockchain is generated, referring to FIG. 6c, when a node in which the blockchain is located receives the input information, the node verifies the input information; after the verification is completed, stores the input information in a memory pool, and updates a hash tree used for recording the input information; and then, updates an updated timestamp the time when the input information is received, tries different random numbers, and performs feature value calculation a plurality of times, so that the calculated feature value may meet the following formula:

$$SHA256(SHA256(version+prev\_hash+merkle\_root+ntime+nbits+x))<TARGET$$

where SHA256 represents a feature value algorithm for calculating the feature value; version represents version information of a relevant block protocol in the blockchain; prev_hash represents the block header feature value of the parent block of the current block; merkle_root represents the feature value of the input information; ntime represents the update time when the timestamp is updated; nbits represents the current difficulty, which is a fixed value within a period of time, and will be determined again after a fixed period of time has passed; x represents the random number; and TARGET represents a feature value threshold, which may be determined according to nbits.

In this case, when the random number that meets the above formula is calculated, the information may be correspondingly stored to generate the block header and the block body to obtain the current block. Subsequently, the node in which the blockchain is located sends, according to node identifiers of other nodes in the data sharing system, a newly generated block to the other nodes in the data sharing system in which the node is located, the newly generated block is verified by the other nodes, and after the verification is completed, the newly generated block is added to the blockchain stored in the nodes.

In certain embodiments of the present disclosure, the prediction result may be stored in the blockchain to prevent the prediction result from being tampered with, which improves credibility of the property prediction.

A person of ordinary skill in the art may understand that, all or some steps of the methods of the foregoing embodiments may be implemented through instructions, or implemented through instructions controlling relevant hardware, and the instructions may be stored in a computer-readable storage medium and loaded and executed by a processor.

To this end, certain embodiments of the present disclosure provide a computer-readable storage medium storing a computer program, and the computer program can be loaded by a processor to perform the steps in any one of the compound property prediction methods according to certain embodiments of the present disclosure. For example, the computer program may perform the following steps:

Chemical structure information of a target compound is obtained, where the chemical structure information includes an atom and a chemical bond; a chemical structure graph corresponding to the chemical structure information is generated according to the chemical structure information, where the chemical structure graph includes a node corresponding to the atom and an edge corresponding to the chemical bond; an original node feature of the node and an original edge feature of the edge are constructed; a plurality of rounds of message propagation are performed on the edge according to the original node feature of the node and the original edge feature of the edge to obtain propagation state information of the edge after the plurality of rounds of message propagation; a target feature of the edge is obtained according to the propagation state information; and properties of the target compound are predicted according to the target feature of the edge, and a property prediction result of the target compound is outputted; or chemical structure information of a target compound is obtained, where the chemical structure information includes an atom and a chemical bond; a chemical structure graph corresponding to the chemical structure information is generated according to the chemical structure information, where the chemical structure graph includes a node corresponding to the atom and an edge corresponding to the chemical bond; initial input information of the multi-layer edge information propagation model is obtained according to an original node feature vector of the node and an original edge feature vector of the edge; a plurality of rounds of message propagation are performed on the edge based on the initial input information by using the multi-layer edge information propagation model, to obtain propagation state information of the edge after the plurality of rounds of message propagation; a target feature of the edge is obtained based on the propagation state information by using the multi-layer edge information propagation model; and properties of the target compound are predicted according to the target feature of the edge by using the multi-layer edge information propagation model, and a property prediction result of the target compound is outputted.

For specific implementations of the above operations, refer to the foregoing embodiments. Details are not described herein again.

The computer-readable storage medium may include: a read-only memory (ROM), a random access memory (RAM), a magnetic disk, an optical disc or the like.

Because the instructions stored in the computer-readable storage medium may perform the steps of any compound property prediction method provided in the embodiments of present disclosure, the instructions can implement beneficial effects that may be implemented by any compound property prediction method provided in the embodiments of present disclosure. For details, refer to the foregoing embodiments. Details are not described herein again.

A compound property prediction method and apparatus, a computing device, and a computer-readable storage medium provided in certain embodiments of the present disclosure are described above in detail. Although the principles and implementations of certain embodiments of the present disclosure are described by using specific examples in this specification, the descriptions of the foregoing embodiments are merely intended to help understand the method and the idea of the method according to certain embodiments of the present disclosure. Meanwhile, a person skilled in the art may make modifications to the specific implementations and application range according to the idea of the present disclosure. In conclusion, the content of this specification is not to be construed as a limitation to the present disclosure.

What is claimed is:

1. A compound property prediction method performed by an electronic device, the method comprising:
   obtaining chemical structure information of a target compound, the chemical structure information including an atom and a chemical bond;
   modeling a chemical structure graph according to the chemical structure information, the chemical structure graph including a first node corresponding to the atom and a first edge corresponding to the chemical bond;
   constructing an original node feature of the first node and an original edge feature of the first edge;
   performing a message propagation on the first edge according to the original node feature of the first node and the original edge feature of the first edge to obtain propagation state information of the first edge; and
   predicting properties of the target compound according to the propagation state information of the first edge.

2. The compound property prediction method according to claim 1, wherein the performing the message propagation on the first edge according to the original node feature of the first node and the original edge feature of the first edge to obtain propagation state information of the first edge comprises:
   obtaining initial input information of the message propagation according to the original node feature of the first node and the original edge feature of the first edge; and
   performing the message propagation on the first edge based on the initial input information to obtain the propagation state information of the first edge.

3. The compound property prediction method according to claim 2, wherein the performing the message propagation on the first edge based on the initial input information to obtain the propagation state information of the first edge comprises:
   using the initial input information as a current input to a current round of message propagation, and performing the current round of message propagation based on the current input;
   obtaining current propagation state information of the first edge during the current round of message propagation according to the original node feature of the first node, a current edge feature of the first edge, and historical propagation state information, the historical propagation state information being propagation state information of the first edge during a historical round of message propagation; and updating the current input according to the current propagation state information and the original node feature of the first node no later than entering a next round of message propagation, and returning to performing the current round of message propagation based on the current input until all rounds of message propagation are completed, to obtain the propagation state information of the first edge.

4. The compound property prediction method according to claim 3, wherein the first node is either a start node or an end node, wherein the first edge is defined by the start node and the end node, and wherein the obtaining current propagation state information of the first edge during the current round of message propagation comprises:

determining at least one in-edge leading to the start node defining the first edge;

aggregating a current edge feature of the at least one in-edge and an original node feature of a node on the in-edge with historical propagation state information of the at least one in-edge during the historical round of message propagation to obtain information of the in-edge;

integrating information of the at least one in-edge to obtain message information of the first edge during the current round of message propagation; and aggregating the historical propagation state information of the first edge during the historical round of message propagation with the message information to obtain the current propagation state information of the first edge during the current round of message propagation.

5. The compound property prediction method according to claim 4, wherein the aggregating a current edge feature of the at least one in-edge and the original node feature of the node on the at least one in-edge with historical propagation state information of the in-edge during the historical round of message propagation to obtain information of the in-edge comprises:

aggregating a current edge feature of the at least one in-edge and an original node feature of a node on the in-edge with historical propagation state information of the in-edge during the historical round of message propagation according to a message generation function to obtain an aggregated feature; and processing the aggregated feature based on a first activation function to obtain the information of the at least one in-edge.

6. The compound property prediction method according to claim 4, wherein the aggregating the historical propagation state information of the first edge during the historical round of message propagation with the message information to obtain the current propagation state information of the first edge during the current round of message propagation comprises:

obtaining referential historical propagation state information of the first edge during a referential historical round of message propagation;

aggregating the referential historical propagation state information with the message information according to a first aggregation parameter to obtain aggregated propagation state information; and processing the aggregated propagation state information based on a second activation function to obtain the current propagation state information of the first edge during the current round of message propagation.

7. The compound property prediction method according to claim 6, wherein the obtaining referential historical propagation state information of the first edge during the referential historical round of message propagation comprises:

aggregating the original edge feature of the first edge with the original node feature of the first node on the first edge according to a second aggregation parameter to obtain an aggregated edge feature of the first edge; and processing the aggregated edge feature based on a third activation function to obtain the referential historical propagation state information of the first edge during the referential historical round of message propagation.

8. The compound property prediction method according to claim 1, wherein the chemical structure graph includes a plurality of nodes, the plurality of nodes including the first node, and wherein the predicting properties of the target compound according to the target feature of the first edge comprises:

converting the target feature of the first edge into a node feature of each of the plurality of nodes in the chemical structure graph;

aggregating the node feature of the each of the plurality of nodes to obtain an aggregated node feature; and predicting the properties of the target compound according to the aggregated node feature.

9. The compound property prediction method according to claim 8, wherein the converting the target feature of the first edge into the node feature of the each of the plurality of nodes in the chemical structure graph comprises:

determining associated edges associated with the each of the plurality of nodes;

aggregating target features of the associated edges to obtain an aggregated associated edge feature; and aggregating a current node feature of the each of the plurality of nodes with the aggregated associated edge feature based on a third aggregation parameter to obtain the node feature of the each of the plurality of nodes.

10. The compound property prediction method according to claim 1, wherein constructing the original node feature of the node and the original edge feature of the edge comprises:

constructing the original node feature of the node according to attribute information of the atom, the attribute information of the atom including one or more of a charge number, a proton number, and a neutron number; and constructing the original edge feature of the edge according to attribute information of the chemical bond, the attribute information of the chemical bond including one or more of a chemical bond type and a chemical bond valence state.

11. The compound property prediction method according to claim 2, wherein the performing the plurality of rounds of message propagation on the first edge based on the initial input information to obtain the propagation state information of the first edge comprises:

importing the initial input information into a multi-layer edge information propagation model, the multi-layer edge information propagation model including a plurality of message propagation layers, a node feature conversion layer, and an aggregation layer; and performing the plurality of rounds of message propagation on the first edge through the plurality of message propagation layers in the multi-layer edge information propagation model to obtain the propagation state information of the first edge.

12. The compound property prediction method according to claim 11, further comprising:

obtaining sample chemical structure information of a sample compound, the sample chemical structure information including a sample atom and a sample chemical bond;

generating a sample chemical structure graph corresponding to the sample chemical structure information according to the sample chemical structure information, the sample chemical structure graph including a sample node corresponding to the sample atom and a sample edge corresponding to the sample chemical bond;

constructing a sample original node feature of the sample node and a sample original edge feature of the sample edge;

predicting, by using a preset multi-layer edge information propagation model, properties of the sample compound based on the sample original node feature of the sample node and the sample original edge feature of the sample edge, to obtain a property prediction result of the sample compound; and calculating a loss between the property prediction result of the sample compound and actual properties based on a loss function, and training the multi-layer edge information propagation model based on the loss, to obtain a trained multi-layer edge information propagation model.

13. A compound property prediction apparatus, comprising: a memory; and a processor coupled to the memory, the processor being positioned to perform:

obtaining chemical structure information of a target compound, the chemical structure information including an atom and a chemical bond;

modeling a chemical structure graph according to the chemical structure information, the chemical structure graph including a first node corresponding to the atom and a first edge corresponding to the chemical bond;

constructing an original node feature of the first node and an original edge feature of the first edge;

performing a message propagation on the first edge according to the original node feature of the first node and the original edge feature of the first edge to obtain propagation state information of the first edge; and predicting properties of the target compound according to the propagation state information of the first edge.

14. The compound property prediction apparatus according to claim 13, wherein the processor is further positioned to perform:

obtaining initial input information of the message propagation according to the original node feature of the first node and the original edge feature of the first edge; and performing the message propagation on the first edge based on the initial input information to obtain the propagation state information of the first edge.

15. The compound property prediction apparatus according to claim 14, wherein the performing the message propagation on the first edge based on the initial input information to obtain the propagation state information of the first edge comprises:

using the initial input information as a current input to a current round of message propagation, and performing the current round of message propagation based on the current input;

obtaining current propagation state information of the first edge during the current round of message propagation according to the original node feature of the first node, a current edge feature of the first edge, and historical propagation state information, the historical propagation state information being propagation state information of the first edge during a historical round of message propagation; and updating the current input according to the current propagation state information and the original node feature of the first node no later than entering a next round of message propagation, and returning to performing the current round of message propagation based on the current input until all rounds of message propagation are completed, to obtain the propagation state information of the first edge.

16. The compound property prediction apparatus according to claim 15, wherein the first node is either a start node or an end node, wherein the first edge is defined by the start node and the end node, and wherein the obtaining current propagation state information of the first edge during the current round of message propagation comprises:

determining at least one in-edge leading to the start node defining the first edge;

aggregating a current edge feature of the at least one in-edge and an original node feature of a node on the in-edge with historical propagation state information of the at least one in-edge during the historical round of message propagation to obtain information of the in-edge;

integrating information of the at least one in-edge to obtain message information of the first edge during the current round of message propagation; and aggregating the historical propagation state information of the first edge during the historical round of message propagation with the message information to obtain the current propagation state information of the first edge during the current round of message propagation.

17. The compound property prediction apparatus according to claim 16, wherein the aggregating a current edge feature of the at least one in-edge and the original node feature of the node on the at least one in-edge with historical propagation state information of the in-edge during the historical round of message propagation to obtain information of the in-edge comprises:

aggregating a current edge feature of the at least one in-edge and an original node feature of a node on the in-edge with historical propagation state information of the in-edge during the historical round of message propagation according to a message generation function to obtain an aggregated feature; and processing the aggregated feature based on a first activation function to obtain the information of the at least one in-edge.

18. The compound property prediction apparatus according to claim 16, wherein the aggregating the historical propagation state information of the first edge during the historical round of message propagation with the message information to obtain the current propagation state information of the first edge during the current round of message propagation comprises:

obtaining referential historical propagation state information of the first edge during a referential historical round of message propagation;

aggregating the referential historical propagation state information with the message information according to a first aggregation parameter to obtain aggregated propagation state information; and processing the aggregated propagation state information based on a second activation function to obtain the current propagation state information of the first edge during the current round of message propagation.

19. The compound property prediction apparatus according to claim 13, wherein the constructing an original node feature of the node and an original edge feature of the edge comprises:
- constructing the original node feature of the node according to attribute information of the atom, the attribute information of the atom including one or more of a charge number, a proton number, and a neutron number; and
- constructing the original edge feature of the edge according to attribute information of the chemical bond, the attribute information of the chemical bond including one or more of a chemical bond type and a chemical bond valence state.

20. A non-transitory computer-readable storage medium storing computer program instructions executable by at least one processor to perform:
- obtaining chemical structure information of a target compound, the chemical structure information including an atom and a chemical bond;
- modeling a chemical structure graph according to the chemical structure information, the chemical structure graph including a first node corresponding to the atom and a first edge corresponding to the chemical bond;
- constructing an original node feature of the first node and an original edge feature of the first edge;
- performing a message propagation on the first edge according to the original node feature of the first node and the original edge feature of the first edge to obtain propagation state information of the first edge; and
- predicting properties of the target compound according to the propagation state information of the first edge.

* * * * *